(12) United States Patent
Warenius et al.

(10) Patent No.: US 8,883,718 B2
(45) Date of Patent: Nov. 11, 2014

(54) TREATING CANCER

(75) Inventors: Hilmar Meek Warenius, Heswall Wirral (GB); William Ure Primrose, Cambridge (GB)

(73) Assignee: Theryte Limited, Lightwater Surrey (GB)

( * ) Notice: Subject to any disclaimer, the term of this patent is extended or adjusted under 35 U.S.C. 154(b) by 489 days.

(21) Appl. No.: 12/922,159

(22) PCT Filed: Mar. 11, 2009

(86) PCT No.: PCT/EP2009/052883
§ 371 (c)(1),
(2), (4) Date: Feb. 4, 2011

(87) PCT Pub. No.: WO2009/112536
PCT Pub. Date: Sep. 17, 2009

(65) Prior Publication Data
US 2011/0158956 A1 Jun. 30, 2011

(30) Foreign Application Priority Data
Mar. 11, 2008 (GB) .................................. 0804496.8

(51) Int. Cl.
A61K 38/12 (2006.01)
C07K 7/64 (2006.01)
C12N 9/12 (2006.01)
A61K 38/00 (2006.01)

(52) U.S. Cl.
CPC ............... C12N 9/1205 (2013.01); A61K 38/00 (2013.01); C07K 2319/00 (2013.01)
USPC ........... 514/1.2; 514/19.9; 514/21.1; 530/321

(58) Field of Classification Search
None
See application file for complete search history.

(56) References Cited

FOREIGN PATENT DOCUMENTS

| EP | 1884521 A | 2/2008 |
| WO | 2003/106491 A2 | 12/2003 |
| WO | 2005123760 A | 12/2005 |
| WO | 2006133566 A | 12/2006 |

OTHER PUBLICATIONS

Fischer et al. Structure-activity relationship of truncated and substituted analogues of the intracellular delivery vector Penetratin. Journal of Peptide Research. 2000, vol. 55, pp. 163-172.*

(Continued)

*Primary Examiner* — Jeffrey E Russel
(74) *Attorney, Agent, or Firm* — Joseph R. Baker, Jr.; Gavrilovich, Dodd & Lindsey LLP

(57) ABSTRACT

Provided is a cyclic peptide which comprises:
(i) a CDK4 peptide region; and
(ii) a cell-penetrating region;
wherein the CDK4 peptide region comprises the amino acid sequence $P^1R^1x^1y^1R^2P^2V$ (SEQ ID NO: 1), in which $P^1$ and $P^2$ are each proline, $R^1$ and $R^2$ are each arginine and each of $x^1$ and $y^1$ are either a linker or proline, wherein if $x^1$ is a linker then $y^1$ is proline or if $x^1$ is proline then $y^1$ is a linker, or wherein $x^1$ and $y^1$ when taken together form a linker, and wherein V may be present or absent; and
wherein the cell-penetrating region is capable of enhancing the uptake of the cyclic peptide or a part thereof into cancer cells and comprises an amphiphilic amino acid sequence; and wherein the cyclic peptide or a part thereof is cytotoxic to and/or inhibiting to the growth of a cancer cell.

35 Claims, 8 Drawing Sheets

THR53

(56) References Cited

OTHER PUBLICATIONS

Van der Schaal, C., International Search Report, PCT/EP2009/052883, European Patent Office, Aug. 20, 2009.

Pujals et al., "Mechanisitic aspects of CPP-mediated intracellular drug delivery: Relevance of CPP self-assembly," Biochimica et Biophysica Acta, Biomembranes, Amsterdam, NL, 2006, pp. 264-279, vol. 1758, No. 3.

European Office Action, EP 09 719 392.4, European Patent Office, Dec. 12, 2013.

* cited by examiner

SEQUENCE LISTING

<160> NUMBER OF SEQ ID NOS: 46

<210> SEQ ID NO 1
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: BINDING
<222> LOCATION: (2)..(3)
<223> OTHER INFORMATION: /note="linker between position 2 and 3 if no linker between position 3 and 4"
<220> FEATURE:
<221> NAME/KEY: BINDING
<222> LOCATION: (3)..(4)
<223> OTHER INFORMATION: /note="linker between position 3 and 4 if no linker between position 2 and 3"

```
<220> FEATURE:
<221> NAME/KEY: VARIANT
<222> LOCATION: (6)..(6)
<223> OTHER INFORMATION: may be present or absent

<400> SEQUENCE: 1

Pro Arg Pro Arg Pro Val
1               5

<210> SEQ ID NO 2
<211> LENGTH: 6
<212> TYPE: PRT
<213> ORGANISM: Artificial Sequence
<220> FEATURE:
<223> OTHER INFORMATION: Cdk4 peptide

<400> SEQUENCE: 2

Pro Arg Gly Pro Arg Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Cdk4 peptide

<400> SEQUENCE: 3

Pro Arg Gly Pro Arg Pro Val
1               5

<210> SEQ ID NO 4
<211> LENGTH: 6
<212> TYPE: PRT
<213> ORGANISM: Artificial Sequence
<220> FEATURE:
<223> OTHER INFORMATION: Cdk4 peptide

<400> SEQUENCE: 4

Pro Arg Pro Gly Arg Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Amphiphilic sequence

<400> SEQUENCE: 5

Ala Leu Lys Leu Ala Leu Lys
1               5

<210> SEQ ID NO 6
<211> LENGTH: 18
<212> TYPE: PRT
<213> ORGANISM: Artificial Sequence
<220> FEATURE:
<223> OTHER INFORMATION: Amphiphilic sequence

<400> SEQUENCE: 6

Lys Leu Ala Leu Lys Leu Ala Leu Lys Ala Leu Lys Ala Ala Leu Lys
1               5                   10                  15

Leu Ala

<210> SEQ ID NO 7
```

```
<211> LENGTH: 10
<212> TYPE: PRT
<213> ORGANISM: Artificial Sequence
<220> FEATURE:
<223> OTHER INFORMATION: Amphiphilic sequence

<400> SEQUENCE: 7

Ala Leu Lys Leu Ala Leu Lys Leu Ala Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Amphiphilic sequence

<400> SEQUENCE: 8

Lys Leu Ala Leu Lys Leu Ala Leu Lys
1               5

<210> SEQ ID NO 9
<211> LENGTH: 18
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(18)
<223> OTHER INFORMATION: /note="cyclic peptide"

<400> SEQUENCE: 9

Pro Arg Gly Pro Arg Pro Val Lys Leu Ala Leu Lys Leu Ala Leu Lys
1               5                   10                  15

Phe Pro

<210> SEQ ID NO 10
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"

<400> SEQUENCE: 10

Pro Arg Gly Pro Arg Pro Val Ala Leu Lys Leu Ala Leu Lys Leu Ala
1               5                   10                  15

Leu

<210> SEQ ID NO 11
<211> LENGTH: 17
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (7)..(17)
<223> OTHER INFORMATION: /note="D amino acids"

<400> SEQUENCE: 11
```

Pro Arg Gly Pro Arg Pro Val Ala Leu Lys Leu Ala Leu Lys Leu Ala
1               5                   10                  15

Leu

<210> SEQ ID NO 12
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (2)..(2)
<223> OTHER INFORMATION: /note="N-methyl arginine"
<220> FEATURE:
<221> NAME/KEY: MISC_FEATURE
<222> LOCATION: (7)..(17)
<223> OTHER INFORMATION: /note="D amino acids"

<400> SEQUENCE: 12

Pro Arg Gly Pro Arg Pro Val Ala Leu Lys Leu Ala Leu Lys Leu Ala
1               5                   10                  15

Leu

<210> SEQ ID NO 13
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (3)..(3)
<223> OTHER INFORMATION: MeGly
<220> FEATURE:
<221> NAME/KEY: MISC_FEATURE
<222> LOCATION: (7)..(17)
<223> OTHER INFORMATION: /note="D amino acids"

<400> SEQUENCE: 13

Pro Arg Gly Pro Arg Pro Val Ala Leu Lys Leu Ala Leu Lys Leu Ala
1               5                   10                  15

Leu

<210> SEQ ID NO 14
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (5)..(5)
<223> OTHER INFORMATION: /note="N-methyl arginine"
<220> FEATURE:
<221> NAME/KEY: MISC_FEATURE
<222> LOCATION: (7)..(17)
<223> OTHER INFORMATION: /note="D amino acids"

```
<400> SEQUENCE: 14

Pro Arg Gly Pro Arg Pro Val Ala Leu Lys Leu Ala Leu Lys Leu Ala
1               5                   10                  15

Leu

<210> SEQ ID NO 15
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (1)..(2)
<223> OTHER INFORMATION: /note="D amino acids"
<220> FEATURE:
<221> NAME/KEY: MISC_FEATURE
<222> LOCATION: (4)..(17)
<223> OTHER INFORMATION: /note="D amino acids"

<400> SEQUENCE: 15

Pro Arg Gly Pro Arg Pro Val Ala Leu Lys Leu Ala Leu Lys Leu Ala
1               5                   10                  15

Leu

<210> SEQ ID NO 16
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (1)..(3)
<223> OTHER INFORMATION: /note="D amino acids"
<220> FEATURE:
<221> NAME/KEY: MISC_FEATURE
<222> LOCATION: (5)..(17)
<223> OTHER INFORMATION: /note="D amino acids"

<400> SEQUENCE: 16

Pro Arg Pro Gly Arg Pro Val Ala Leu Lys Leu Ala Leu Lys Leu Ala
1               5                   10                  15

Leu

<210> SEQ ID NO 17
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (7)..(17)
<223> OTHER INFORMATION: /note="D amino acids"

<400> SEQUENCE: 17
```

```
Pro Arg Gly Pro Arg Pro Val Ala Leu Arg Leu Ala Leu Arg Leu Ala
1               5                   10                  15

Leu

<210> SEQ ID NO 18
<211> LENGTH: 16
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(16)
<223> OTHER INFORMATION: /note="cyclic peptide"
<220> FEATURE:
<221> NAME/KEY: MISC_FEATURE
<222> LOCATION: (7)..(16)
<223> OTHER INFORMATION: /note="D amino acids"

<400> SEQUENCE: 18

Pro Arg Gly Pro Arg Pro Ala Leu Lys Leu Ala Leu Lys Leu Ala Leu
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Cdk4 peptide
<220> FEATURE:
<221> NAME/KEY: VARIANT
<222> LOCATION: (2)..(2)
<223> OTHER INFORMATION: /replace"Thr"/note="if at least one of
      positions 3, 5 and 7 is Pro"
<220> FEATURE:
<221> NAME/KEY: VARIANT
<222> LOCATION: (3)..(3)
<223> OTHER INFORMATION: /replace"Thr"/note="if at least one of
      positions 2, 5 and 7 is Pro"
<220> FEATURE:
<221> NAME/KEY: BINDING
<222> LOCATION: (4)..(5)
<223> OTHER INFORMATION: /note="linker between position 4 and 5"
<220> FEATURE:
<221> NAME/KEY: VARIANT
<222> LOCATION: (5)..(5)
<223> OTHER INFORMATION: /replace"Thr"/note="if at least one of
      positions 2, 3, and 7 is Pro"
<220> FEATURE:
<221> NAME/KEY: VARIANT
<222> LOCATION: (7)..(7)
<223> OTHER INFORMATION: may be present or absent
<220> FEATURE:
<221> NAME/KEY: VARIANT
<222> LOCATION: (7)..(7)
<223> OTHER INFORMATION: /replace"Thr"/note="if at least one of
      positions 2, 3, and 5 is Pro"

<400> SEQUENCE: 19

Phe Pro Pro Arg Pro Arg Pro
1               5

<210> SEQ ID NO 20
<211> LENGTH: 7
<212> TYPE: PRT
<213> ORGANISM: Artificial Sequence
<220> FEATURE:
<223> OTHER INFORMATION: Cdk4 peptide
<220> FEATURE:
<221> NAME/KEY: BINDING
<222> LOCATION: (4)..(5)
<223> OTHER INFORMATION: /note="linker between position 4 and 5"
```

```
<400> SEQUENCE: 20

Phe Pro Pro Arg Pro Arg Pro
1               5

<210> SEQ ID NO 21
<211> LENGTH: 12
<212> TYPE: PRT
<213> ORGANISM: Artificial Sequence
<220> FEATURE:
<223> OTHER INFORMATION: Cdk4 peptide

<400> SEQUENCE: 21

Phe Pro Pro Arg Gly Pro Arg Pro Val Gln Ser Val
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Control peptide

<400> SEQUENCE: 22

Pro Arg Arg Pro Gly Pro
1               5

<210> SEQ ID NO 23
<211> LENGTH: 18
<212> TYPE: PRT
<213> ORGANISM: Artificial Sequence
<220> FEATURE:
<223> OTHER INFORMATION: Control peptide
<220> FEATURE:
<221> NAME/KEY: MISC_FEATURE
<222> LOCATION: (1)..(18)
<223> OTHER INFORMATION: /note="cyclic peptide"

<400> SEQUENCE: 23

Phe Pro Pro Arg Arg Pro Gly Pro Val Lys Leu Ala Leu Lys Leu Ala
1               5                   10                  15

Leu Lys

<210> SEQ ID NO 24
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (8)..(17)
<223> OTHER INFORMATION: /note="D amino acids"

<400> SEQUENCE: 24

Pro Arg Gly Pro Arg Pro Val Ala Leu Lys Leu Ala Leu Lys Leu Ala
1               5                   10                  15

Leu

<210> SEQ ID NO 25
<211> LENGTH: 17
<212> TYPE: PRT
<213> ORGANISM: Artificial Sequence
```

```
-continued

<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (8)..(16)
<223> OTHER INFORMATION: /note="D amino acids"

<400> SEQUENCE: 25

Pro Arg Gly Pro Arg Pro Val Ala Leu Lys Leu Ala Leu Lys Leu Ala
1               5                   10                  15

Leu

<210> SEQ ID NO 26
<211> LENGTH: 17
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MISC_FEATURE
<222> LOCATION: (9)..(16)
<223> OTHER INFORMATION: /note="D amino acids"

<400> SEQUENCE: 26

Pro Arg Gly Pro Arg Pro Val Ala Leu Lys Leu Ala Leu Lys Leu Ala
1               5                   10                  15

Leu

<210> SEQ ID NO 27

<400> SEQUENCE: 27

000

<210> SEQ ID NO 28
<211> LENGTH: 11
<212> TYPE: PRT
<213> ORGANISM: Artificial Sequence
<220> FEATURE:
<223> OTHER INFORMATION: Cdk4 peptide

<400> SEQUENCE: 28

Phe Pro Pro Arg Gly Pro Arg Pro Val Gln Ser
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Cdk4 peptide

<400> SEQUENCE: 29

Pro Arg Gly Pro Arg Pro Val Lys Leu Ala Leu Lys Leu Ala Leu Lys
1               5                   10                  15

Ala Leu

<210> SEQ ID NO 30
<211> LENGTH: 18
```

```
<212> TYPE: PRT
<213> ORGANISM: Artificial Sequence
<220> FEATURE:
<223> OTHER INFORMATION: Control peptide

<400> SEQUENCE: 30

Pro Arg Arg Pro Gly Pro Val Lys Leu Ala Leu Lys Leu Ala Leu Lys
1               5                   10                  15

Ala Leu

<210> SEQ ID NO 31
<211> LENGTH: 18
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(18)
<223> OTHER INFORMATION: /note="cyclic peptide"

<400> SEQUENCE: 31

Gly Gly Gly Gly Gly Gly Pro Arg Gly Pro Arg Pro Gly Gly Gly Gly
1               5                   10                  15

Gly Gly

<210> SEQ ID NO 32
<211> LENGTH: 18
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(18)
<223> OTHER INFORMATION: /note="cyclic peptide"

<400> SEQUENCE: 32

Ala Ala Ala Gly Gly Gly Pro Arg Gly Pro Arg Pro Gly Gly Gly Ala
1               5                   10                  15

Ala Ala

<210> SEQ ID NO 33
<211> LENGTH: 28
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(28)
<223> OTHER INFORMATION: /note="cyclic peptide"

<400> SEQUENCE: 33

Gly Gly Gly Gly Pro Arg Gly Pro Arg Pro Gly Gly Gly Gly Pro Arg
1               5                   10                  15

Gly Pro Arg Pro Val Pro Arg Gly Pro Arg Pro Val
            20                  25

<210> SEQ ID NO 34
<211> LENGTH: 18
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
```

```
<222> LOCATION: (1)..(18)
<223> OTHER INFORMATION: /note="cyclic peptide"

<400> SEQUENCE: 34

Ala Ala Gly Pro Gly Gly Pro Arg Gly Pro Arg Pro Gly Gly Pro Gly
1               5                   10                  15

Ala Ala

<210> SEQ ID NO 35
<211> LENGTH: 21
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(21)
<223> OTHER INFORMATION: /note="cyclic peptide"

<400> SEQUENCE: 35

Pro Arg Gly Pro Arg Pro Val Pro Arg Gly Pro Arg Pro Val Pro Arg
1               5                   10                  15

Gly Pro Arg Pro Val
            20

<210> SEQ ID NO 36
<211> LENGTH: 16
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(16)
<223> OTHER INFORMATION: /note="cyclic peptide"

<400> SEQUENCE: 36

Pro Arg Gly Pro Arg Pro Ala Leu Lys Leu Ala Leu Lys Leu Ala Leu
1               5                   10                  15

<210> SEQ ID NO 37
<211> LENGTH: 18
<212> TYPE: PRT
<213> ORGANISM: Artificial Sequence
<220> FEATURE:
<223> OTHER INFORMATION: Cdk4 peptide

<400> SEQUENCE: 37

Arg Gly Ala Phe Pro Pro Arg Gly Pro Arg Pro Val Gln Ser Val Val
1               5                   10                  15

Pro Glu

<210> SEQ ID NO 38
<211> LENGTH: 18
<212> TYPE: PRT
<213> ORGANISM: Artificial Sequence
<220> FEATURE:
<223> OTHER INFORMATION: Cdk6 peptide

<400> SEQUENCE: 38

Arg Gln Ala Phe His Ser Lys Ser Ala Gln Pro Ile Glu Lys Phe Val
1               5                   10                  15

Thr Asp

<210> SEQ ID NO 39
```

```
<211> LENGTH: 18
<212> TYPE: PRT
<213> ORGANISM: Artificial Sequence
<220> FEATURE:
<223> OTHER INFORMATION: Cdk2 peptide

<400> SEQUENCE: 39

Lys Pro Ser Phe Pro Lys Trp Ala Arg Gln Asp Phe Ser Lys Val Val
1               5                   10                  15

Pro Pro

<210> SEQ ID NO 40
<211> LENGTH: 6
<212> TYPE: PRT
<213> ORGANISM: Artificial Sequence
<220> FEATURE:
<223> OTHER INFORMATION: Cdk4 peptide
<220> FEATURE:
<221> NAME/KEY: VARIANT
<222> LOCATION: (1)..(1)
<223> OTHER INFORMATION: /replace"Thr"/note="if at least one of
      positions 4 and 6 is Pro"
<220> FEATURE:
<221> NAME/KEY: VARIANT
<222> LOCATION: (1)..(1)
<223> OTHER INFORMATION: may be absent if position 6 is present
<220> FEATURE:
<221> NAME/KEY: VARIANT
<222> LOCATION: (4)..(4)
<223> OTHER INFORMATION: /replace"Thr"/note="if at least one of
      positions 1 and 6 is Pro"
<220> FEATURE:
<221> NAME/KEY: VARIANT
<222> LOCATION: (6)..(6)
<223> OTHER INFORMATION: /replace"Thr"/note="if at least one of
      positions 1 and 4 is Pro"
<220> FEATURE:
<221> NAME/KEY: VARIANT
<222> LOCATION: (6)..(6)
<223> OTHER INFORMATION: may be absent if position 1 is present

<400> SEQUENCE: 40

Pro Arg Gly Pro Arg Pro
1               5

<210> SEQ ID NO 41
<211> LENGTH: 10
<212> TYPE: PRT
<213> ORGANISM: Artificial Sequence
<220> FEATURE:
<223> OTHER INFORMATION: Amphiphilic Sequence

<400> SEQUENCE: 41

Ala Leu Arg Leu Ala Leu Arg Leu Ala Leu
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (2)..(2)
<223> OTHER INFORMATION: /note="N-methyl arginine"

<400> SEQUENCE: 42
```

Pro Arg Gly Pro Arg Pro Val Ala Leu Lys Leu Ala Leu Lys Leu Ala
1               5                   10                  15

Leu

<210> SEQ ID NO 43
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (3)..(3)
<223> OTHER INFORMATION: MeGly

<400> SEQUENCE: 43

Pro Arg Gly Pro Arg Pro Val Ala Leu Lys Leu Ala Leu Lys Leu Ala
1               5                   10                  15

Leu

<210> SEQ ID NO 44
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"
<220> FEATURE:
<221> NAME/KEY: MOD_RES
<222> LOCATION: (5)..(5)
<223> OTHER INFORMATION: /note="N-methyl arginine"

<400> SEQUENCE: 44

Pro Arg Gly Pro Arg Pro Val Ala Leu Lys Leu Ala Leu Lys Leu Ala
1               5                   10                  15

Leu

<210> SEQ ID NO 45
<211> LENGTH: 17
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(17)
<223> OTHER INFORMATION: /note="cyclic peptide"

<400> SEQUENCE: 45

Pro Arg Gly Pro Arg Pro Val Ala Leu Arg Leu Ala Leu Arg Leu Ala
1               5                   10                  15

Leu

<210> SEQ ID NO 46
<211> LENGTH: 8
<212> TYPE: PRT
<213> ORGANISM: Artificial Sequence
<220> FEATURE:
<223> OTHER INFORMATION: Cyclic peptide
<220> FEATURE:

```
<221> NAME/KEY: BINDING
<222> LOCATION: (4)..(5)
<223> OTHER INFORMATION: /note="linker between position 4 and 5 if no
      linker between position 5 and 6"
<220> FEATURE:
<221> NAME/KEY: BINDING
<222> LOCATION: (5)..(6)
<223> OTHER INFORMATION: /note="linker between position 5 and 6 if no
      linker between position 4 and 5"
<220> FEATURE:
<221> NAME/KEY: VARIANT
<222> LOCATION: (8)..(8)
<223> OTHER INFORMATION: may be present or absent

<400> SEQUENCE: 46

Phe Pro Pro Arg Pro Arg Pro Val
1               5
```

TREATING CANCER

CROSS REFERENCE TO RELATED APPLICATIONS

This application is a U.S. National Stage Application filed under 35 U.S.C. §371 and claims priority to International Application No. PCT/EP2009/052883, filed Mar. 11, 2009, which application claims priority to Great Britain Application No. 0804496.8, filed on Mar. 11, 2008, the disclosure of which are incorporated herein by reference.

FIELD OF THE INVENTION

The present invention relates to peptides and mimetic compounds that are cytotoxic to, and/or inhibiting to the growth of, a cancer cell and/or stimulating to the growth of a non-cancerous cell and/or a control cell. The present invention also relates to medical uses of such peptides and mimetics.

BACKGROUND TO THE INVENTION

Although chemotherapy has been responsible for curing many people of cancer, there still remain a large number of patients whose tumours either show little response to treatment, or respond initially only to recur later. For these patients the current treatments are clearly inadequate.

It is thought that certain tumours are unresponsive to conventional chemotherapy because the cells of these tumours have a pattern of gene expression that renders them insensitive to chemotherapeutic agents. Similarly, it is thought that tumours often respond initially to chemotherapy, but subsequently become resistant because the cells of the tumour exhibit tumour heterogeneity and genetic instability. Tumour heterogeneity describes the situation where different cells in the tumour have different patterns of gene expression with some cells being resistant to a chemotherapeutic agent, whilst other cells are sensitive to this agent. Treating such a tumour with this chemotherapeutic agent therefore kills the sensitive cells, resulting in tumour shrinkage, but fails to kill the resistant cells, which continue dividing to produce a cancer that is wholly drug resistant.

In addition, most conventional chemotherapeutic agents developed up to the present time generally inhibit the growth of important normal cells, for example: a) chemotherapeutic inhibition of the progenitor cells of the haemopoietic system resulting in a fall of red blood cells, white blood cells and platelets causing anaemia, susceptibility to infection and spontaneous bleeding b) inhibition of replacement of normal cells in the bowel causing diarrhoea or c) inhibition of replacement of squamous cells lining the mouth, nose and throat etc.

Genetic instability is found in the majority of cancers. It results in the tumour cells acquiring new mutations. Certain of these mutations may confer drug resistance to the cells in which they occur. These drug resistant cells survive chemotherapy and divide to produce a cancer that is drug resistant.

There is thus a need for anticancer agents which are effective against all cancer cells, which are not affected by tumour heterogeneity and genetic instability and which do not inhibit growth of normal (non-cancerous) cells or which may even promote normal non-cancerous cell growth.

WO 03/081239, which is hereby incorporated in its entirety by reference, identifies gene products, termed critical normal gene products, which are required for cancer cell survival and proliferation. Because critical normal gene products are required for cancer cell survival and proliferation, they must be present and functioning in every tumour cell and therefore provide a consistent anti-cancer drug target that is unaffected by tumour heterogeneity and genetic instability. WO 03/081239 teaches that agents that disrupt critical normal gene products provide effective anti-cancer agents. Although generic methods for disrupting critical normal gene products were disclosed, WO 03/081239 did not disclose any agent that could successfully treat cancer.

Critical normal gene products should also, by definition, not disrupt the function of normal cells. Thus, conventional chemotherapy in the clinic is non-selective and thus consistently damages normal non-cancerous cells and is only effective against non-resistant cancer cells.

An ideal anticancer agent would inhibit the growth of most, if not all, types of cancer cell growth but have no effect on, or even stimulate, normal non-cancerous cell growth.

WO 03/081239 identified CDK4 protein as a critical normal gene product that is present in most (if not all) cancers.

CDK4 protein is known to regulate entry into S phase of the cell cycle by initiating the events needed for the cell to enter S phase. More particularly, activated CDK4 phosphorylates pRb and related proteins p107 and p130. In their hypophosphorylated state these proteins bind E2F transcription factors. However, upon phosphorylation, the E2F transcription factors are released as heterodimers with the proteins DP-1/DP-2. The E2F/DP heterodimers then bind to DNA and activate factors required for DNA synthesis (an activity that takes place during S phase). In addition, free E2F protein upregulates genes controlling cell division such as cyclin E, cyclin A, CDK1 and E2Fs, thereby progressing the cell cycle.

CDK4 protein is only activated when conditions for entry into S phase are suitable and positive signal transduction pathways relaying signals from cell surface receptors such as the Ras/Raf/Erk pathway have been demonstrated to affect CDK4 activation. CDK4 protein is activated by phosphorylation of threonine 164 but inhibited by phosphorylation of tyrosine 17.

To enable it to perform its role, CDK4 protein is known to have many functions including binding cyclin D1, phosphorylating pRb, binding to CDK inhibitors such as p21, p27, p16, binding to cyclin activating kinase and interacting with the enzymes responsible for phosphorylating and dephosphorylating tyrosine 17.

Because of its role in promoting cell division, several studies have investigated the role of CDK4 protein in cancer.

Knockout mice lacking CDK4 protein do not develop cancer following induction with a classical system of initiator (DMBA) followed by promoter (TBA i.e. phorbol ester) (Robles et al. (1998) Genes Dev. 12: 2469; Rodriguez-Puebla et al. (2002) Am. J. Path. 161: 405). No other knockout (including a cyclin D1 knockout) has such a marked effect on cancer development.

However, the CDK4 protein is typically over-expressed in cancer cells. In addition, transgenic mice overexpressing CDK4 protein are more readily induced to develop cancer using the carcinogenesis induction system mentioned above (Robles et al. (1998) Genes Dev. 12: 2469; Rodriguez-Puebla et al. (2002) Am. J. Path. 161: 405).

Moreover, transfection of normal CDK4 has been shown to cause extension of proliferative lifespan in normal human fibroblasts (Morris et al. (2002) Oncogene 21, 4277)

In view of the apparent importance of CDK4 protein in cancer, it has been proposed to be an anticancer target. However, drugs that inhibit CDK4 kinase activity (such as flavopiridol) have very little clinical effect in phase II studies.

WO2005/123760 provides peptides which comprise an amino acid sequence that is part of the amino acid sequence of CDK4 protein or homologous to a part of that amino acid sequence. The peptides are cytotoxic to and/or inhibiting to the growth of a cancer cell. Various linear and cyclic peptides are described in this document. This document discloses amino acid sequences having the general formula YRGXRY (SEQ ID NO: 40) wherein R is arginine and G is glycine, Y may be present or absent, at least one Y is present, X and Y are proline or threonine and at least one X and/or Y is proline. For example, the hexameric peptide PRGPRP (SEQ ID NO: 2) was found to have selective killing activity on human cancer cells but not normal human fibroblasts.

Further the peptides according to WO2005/123760 may be linear or cyclic and may comprise m further amino acid sequences, each further amino acid sequence independently having z amino-acids, wherein m is an integer from 0-10 and z is an integer from 1-20.

A disadvantage with such peptides is that they are limited in their applicability to therapy because specific activity was found to be relatively low. Accordingly, there is a need to find improved compounds which retain their selective killing activity on human cancer cells but whose specific activity is improved.

SUMMARY OF INVENTION

In a first aspect, the present invention provides a cyclic peptide which comprises:
(i) a CDK4 peptide region; and
(ii) a cell-penetrating region;
wherein the CDK4 peptide region comprises the amino acid sequence $P^1R^1x^1y^1R^2P^2V$ (SEQ ID NO: 1), in which $P^1$ and $P^2$ are each proline, $R^1$ and $R^2$ are each arginine and each of $x^1$ and $y^1$ are either a linker or proline, wherein if $x^1$ is a linker then $y^1$ is proline or if $x^1$ is proline then $y^1$ is a linker, or wherein $x^1$ and $y^1$ when taken together form a linker, and wherein V may be present or absent; and
wherein the cell-penetrating region is capable of enhancing the uptake of the cyclic peptide or a part thereof into cancer cells and comprises an amphiphilic amino acid sequence; and
wherein the cyclic peptide or a part thereof is cytotoxic to and/or inhibiting to the growth of a cancer cell.

Preferably, the cell-penetrating region is capable of enhancing the uptake of the CDK4 peptide region.

It has surprisingly been found that by providing a cyclic peptide having the particular features recited above, selective cell killing activity at a higher specific activity can be achieved. This enables a far lower drug dose to be used in the treatment of cancer than was hitherto possible.

The CDK4 peptide region comprises the above amino acid sequence which is part of the amino acid sequence of a CDK4 protein or homologous to part of the amino acid sequence of CDK4 protein. Whilst sub-sequences of the CDK4 protein have been proposed in WO2005/123760 for use as an anti-cancer agent, the cyclic peptides described in the present application have been surprisingly found to be substantially more effective as agents for treating cancer than the linear and cyclic peptides disclosed in WO2005/123760.

The cell penetrating region is capable of enhancing the uptake of the CDK4 peptide region into cancer cells. Uptake may be readily tested by exposing cells to the peptide agent, washing excess/external agent from the cell surface by centrifugation and resuspension in phosphate buffered saline at four degrees centigrade, making a lysate of the remaining cell pellet and detecting the agent by HPLC and mass spectroscopy.

The cell-penetrating region comprises an amphiphilic amino acid sequence. The amphiphilic sequence facilitates uptake into cells.

Amphipathic cell-penetrating peptides are known in the art. Magzouba and Gräslund discuss cell penetrating peptides generally in Quarterly Reviews of Biophysics 37, 2 (2004) pages 147 to 195. In this review primary amphipathic cell-penetrating peptides include MAPs, which are model amphipathic peptides. These are described as linear peptides in this review article. For additional references regarding amphipathic peptides see Oehlke, J., Krause, E., Wiesner, B., Beyermann, M. & Bienert, M. (1996) Nonendocytic, amphipathicity dependent cellular uptake of helical model peptides. Protein Pept. Lett. 3, 393-398; Oehlke, J., Scheller, A., Wiesner, B., Krause, E., Beyermann, M., Klauschenz, E., Melzig, M. & Bienert, M. (1998), Cellular uptake of an alpha-helical amphipathic model peptide with the potential to deliver polar compounds into the cell interior non-endocytically. Biochim. Biophys. Acta 1414, 127-139; Scheller, A., Oehlke, J., Wiesner, B., Dathe, M., Krause, E., Beyermann, M., Melzig, M. & Bienert, M. (1999) Structural requirements for cellular uptake of alpha-helical amphipathic peptides. J. Pept. Sci. 5, 185-194.

It has been surprisingly found that a peptide having the combination of features of comprising the amino acid sequence $P^1R^1x^1y^1R^2P^2V$ (SEQ ID NO: 1) from CDK4, comprising a cell-penetrating region which comprises an amphiphilic sequence and being cyclic provides selective cell killing activity at a higher specific activity than agents known in the art. In particular, the peptides according to the invention rely on the combination of cyclisation and an amphiphilic sequence; peptides comprising the $P^1R^1x^1y^1R^2P^2V$ sequence (SEQ ID NO: 1) which are linear and further comprise an amphiphilic sequence or peptides comprising the $P^1R^1x^1y^1R^2P^2V$ sequence (SEQ ID NO: 1) which are cyclic but do not comprise the amphiphilic sequence are less effective than the peptides according to the present invention which comprise all of these features.

The linker is not especially limited, provided it can join $P^1R^1$ to $y^1R^2P^2V$ (if $x^1$ is the linker) or $P^1R^1x^1$ to $R^2P^2V$ (if it is the linker), or $P^1R^1$ to $R^2P^2V$ if $x^1y^1$ together form a linker. Many examples of suitable chemical groups for providing such a linker are well known in the art. The linker may comprise $C_1$ to $C_4$ hydrocarbylene or an amino acid. Preferably the amino acid is a non-polar amino acid, i.e. alanine, cysteine, glycine, isoleucine, leucine, methionine, phenylalanine, proline, tryptophan or valine. Most preferably, the linker is glycine. Preferably $x^1$ is glycine and $y^1$ is proline, i.e. the CDK4 peptide region comprises the sequence PRGPRP (SEQ ID NO: 2). In a more preferred embodiment the CDK4 peptide region comprises the sequence PRGPRPV (SEQ ID NO: 3). In an alternative embodiment the CDK4 peptide region comprises the sequence PRPGRP (SEQ ID NO: 4).

The inventors have found that the length of the amphiphilic sequence in the cyclic peptide has an effect on PRGPRP (SEQ ID NO: 2) anticancer function. Without being bound by theory, it is understood that the amphiphilic sequences provide rigidity, limiting the freedom of movement of the ends of PRGPRP (SEQ ID NO: 2). Thus it is believed that by altering the length of the amphiphilic peptide sequence, PRGPRP (SEQ ID NO: 2) can be held in an optimal structural conformation to present the two arginines most efficiently to PRGPRP (SEQ ID NO: 2) receptor sites, for example downstream protein SH3 regions.

In a particularly preferred embodiment the amphiphilic amino acid sequence is 9 or 10 amino acids in length.

It is preferable that the amphiphilic amino acid sequence comprises ALKLALK (SEQ ID NO: 5). These sequences are amphiphilic sub-sequences of KLALKLALKAL-KAALKLA (SEQ ID NO: 6).

In one embodiment the amphiphilic amino acid sequence comprises ALKLALKLAL (SEQ ID NO: 7). In a particular embodiment the amphiphilic amino acid sequence consists of ALKLALKLAL (SEQ ID NO: 7) i.e. the sequence is 10 amino acids in length.

In another embodiment the amphilic amino acid sequence is 9 amino acids in length, and the cyclic peptide further comprises a dipeptide spacer linking the CDK4 peptide region and the cell-penetrating region. Typically, the dipeptide spacer is FP, wherein the proline is attached to the N-terminal side of the sequence $P^1R^1x^1y^1R^2P^2V$ (SEQ ID NO: 1). Preferably, the amphiphilic amino acid sequence comprises KLALKLALK (SEQ ID NO: 8).

In these sequences the lysine (K) residues are charged and the leucine and alanine residues are hydrophobic. It is thought that this combination of hydrophilic/hydrophobic residues gives rise to the amphiphilic properties needed to render the cyclic peptide capable of being taken up into cancer cells thereby enhancing the uptake of the CDK4 peptide region.

In some embodiments the amphiphilic amino acid sequence comprises ALRLALRLAL (SEQ ID NO: 41).

In one embodiment, a glycine or arginine residue in the amino acid sequence $P^1R^1x^1y^1R^2P^2V$ (SEQ ID NO: 1) is methylated on the backbone amide nitrogen. Preferably, $R^1$ or $R^2$ is methylated on the backbone amide nitrogen. $x^1$ may be glycine which is methylated on the backbone amide nitrogen. N-methyl glycine is also known as sarcosine. Other modifications of the amino acid residues of the peptide sequences can be anticipated.

The inventors have also discovered that the stereochemistry of the cyclic peptide has an impact on the effectiveness in being cytotoxic to and/or inhibiting to the growth of a cancer cell. In one embodiment each amino acid is the L stereoisomer. In another embodiment at least one amino acid is the D stereoisomer.

It may be that each amino acid of the amphiphilic sequence is the D stereoisomer. In one embodiment each amino acid of the CDK4 peptide region is the L stereoisomer. In a particular embodiment each amino acid of the amphiphilic sequence is the D stereoisomer and each amino acid of the CDK4 peptide region is the L stereoisomer.

In another embodiment of the invention at least one amino acid of the CDK4 peptide region is the D stereoisomer. Preferably, the valine residue of the amino acid sequence $P^1R^1x^1y^1R^2P^2V$ of the CDK4 peptide region is the D stereoisomer. More preferably, each of $P^1$, $R^1$, $R^2$, and $P^2$ is the D stereoisomer and either $x^1$ or $y^1$ is D-proline.

Particularly preferred peptides of the invention are cyc-[PRGPRPVKLALKLALKFP] (SEQ ID NO: 9, THR 53); cyc-[PRGPRPVALKLALKLAL] (SEQ ID NO: 10, THR 54); cyc-[PRGPRPvalklalklal] (SEQ ID NO: 11, THR 79); cyc-[P(N-Me-Arg)GPRPvalklalklal] (SEQ ID NO: 12, THR 80); cyc-[PR(N-Me-Gly)PRPvalklalklal] (SEQ ID NO: 13, THR 81); cyc-[PRGP(N-Me-Arg)Pvalklalklal] (SEQ ID NO: 14, THR 82); cyc-[prGprpvalklalklal] (SEQ ID NO: 15, THR 83); cyc-[prpGrpvalklalklal] (SEQ ID NO: 16, THR 84); cyc-[PRGPRPvalrlalrlal] (SEQ ID NO: 17, THR 85); cyc-[PRGPRPalklalklal] (SEQ ID NO: 18, THR 86), wherein the notation "cyc" refers to a cyclic peptide, upper case denotes the L stereoisomer and lower case denotes the D stereoisomer. "N-Me-Arg" denotes N-methyl arginine and "N-Me-Gly" denotes N-methyl glycine (sarcosine). Variations on these peptides can be envisioned, and in particular, peptides with different stereochemistry may be provided.

According to another aspect of the invention is provided a cyclic peptide which comprises:
  (i) a CDK4 peptide region; and
  (ii) a cell-penetrating region;
wherein the CDK4 peptide region comprises the amino acid sequence FXXRZXRY (SEQ ID NO: 19), in which F is phenylalanine, R is arginine, Z is a linker, X and Y are proline or threonine, Y may be present or absent and at least one of X and/or Y is proline;
wherein the cell-penetrating region comprises a moiety capable of enhancing the uptake of the CDK4 peptide region into cancer cells; and wherein the cyclic peptide is cytotoxic to and/or inhibiting to the growth of a cancer cell.

Again, it has surprisingly been found that by providing a cyclic peptide having the particular features recited above, selective cell killing activity at a higher specific activity can be achieved. This enables a far lower drug dose to be used in the treatment of cancer than was hitherto possible. In this aspect of the invention, it has been found that the FX dipeptide spacer is particularly important for efficacy of the sequence.

In this aspect of the invention it is preferred that Y is present in the CDK4 peptide region and more preferred that both X and Y are proline residues. A preferred sequence for CDK4 peptide region is therefore FPPRZPRP (SEQ ID NO: 20).

Z is present as a linker in the region so as to separate the arginine residue from the X residue. Z is preferably glycine but may be other polar amino acids or may be C1 to C4 hydrocarbylene. Other linkers incorporating hetero atoms and other functionalities may be used provided that they do not interfere with the anti-cancer function of the CDK4 peptide region. The linker is therefore preferably inert.

The cell penetrating region comprises a moiety capable of enhancing the uptake of the CDK4 peptide region into cancer cells. Uptake may be readily tested by exposing cells to the peptide agent, washing excess/external agent from the cell surface by centrifugation and resuspension in phosphate buffered saline at four degrees centigrade, making a lysate of the remaining cell pellet and detecting the agent by HPLC and mass spectroscopy.

The cell-penetrating region preferably comprises a peptide. The cell-penetrating region is preferably an amphiphilic region so as to facilitate uptake into cells. The peptide may be particularly useful as an amphiphilic region because it may be composed of both hydrophobic and hydrophilic residues.

Amphipathic cell-penetrating peptides are known in the art (see discussion above). Magzouba and Gräslund discuss cell penetrating peptides generally in Quarterly Reviews of Biophysics 37, 2 (2004) pages 147 to 195. In this review primary amphipathic cell-penetrating peptides include MAPs, which are model amphipathic peptides. These are described as linear peptides in this review article.

In the second aspect of the present invention, the amphiphilic region preferably comprises KLALKLALKAL-KAALKLA (SEQ ID NO: 6) or an amphiphilic sub-sequence thereof. A preferred amphiphilic sub-sequence is KLA-LKLALK (SEQ ID NO: 8). Other sub-sequences may be used in the amphiphilic region. In these sequences the lysine (K) residues are charged and the leucine and alanine residues are hydrophobic. It is thought that this combination of hydrophilic/hydrophobic residues gives rise to the amphiphilic properties needed to render the cyclic peptide capable of being taken up into cancer cells thereby enhancing the uptake of the CDK4 peptide region.

Other cell penetrating regions may be used in the second aspect of the present invention and these are also discussed in the Magzouba and Gräslund review. Regions comprising penetratins, peptides of the tat family, chimeric cell-penetrating peptides, antimicrobial-derived cell penetrating peptides, neuropeptide-derived cell penetrating peptides, peptides from the prion family and other cell penetrating peptides may be used. These are set out in Table 1 on page 150 of the Magzouba and Gräslund review.

Advantageously, the CDK4 peptide region further comprises a valine residue (V) attached to the C-terminal end thereof. The purpose of this V residue is to link the CDK4 peptide region to the cell-penetrating region.

In all embodiments the peptide of the present invention is cytotoxic to, or inhibiting to the growth of, a cancer cell and/or stimulating to the growth of a non-cancerous and/or control cell. In this context, a cancer cell is a cell taken from a primary tumour, a metastasis or other suspected site of cancer in a subject, or a cell line derived from a cancer. It is preferred that the peptide is more cytotoxic to, or more inhibiting to the growth of a cancer cell than a non-cancerous cell and/or a control cell. In a preferred embodiment of the present invention the peptide is non-inhibitory to the growth of non-cancerous cells and/or control cells.

In the context of this invention, non-cancerous cells are any normal (healthy) cells i.e. cells not affected by cancer and may be cells of any tissue of a patient. A control cell includes a normal non-cancerous cell used to measure cytotoxicity against and may be derived from the corresponding normal tissue of a patient, from any other normal tissue of a patient or from a primary cell culture. Thus, in many cases a non-cancerous cell and a control cell may be the same, both being a normal healthy cell. Typically, human fibroblasts or keratinocytes in short term primary culture are non-cancerous cells and used as control cells.

Cancer cells can be identified by measuring the expression levels of the CDK1 and CDK4 gene products, as disclosed in WO99/42821. A cell sample is cancerous if the ratio of the expression levels of the CDK1 and CDK4 proteins is in the range 0.6 to 1.6.

The invention also provides mimetic compounds capable of functionally mimicking peptides according to the invention, which mimetics are cytotoxic to, or inhibiting to the growth of a cancer cell. It is preferred that the mimetic compound is more cytotoxic to, or more inhibiting to the growth of a cancer cell than a non-cancerous cell and/or a control cell. In a preferred embodiment the mimetic compound is non-inhibitory to the growth of normal non-cancerous cells and/or control cells. Optionally, the mimetic compound stimulates the growth of normal non-cancerous cells and/or control cells. The mimetic compound may be a peptidomimetic, which may comprise one or more amide bonds in its molecular backbone, or a non-peptide mimetic, which does not.

In a further aspect of the invention, medical uses of the peptides and mimetics are provided. For example, the invention provides a pharmaceutical composition comprising a peptide or mimetic compound as described above and a carrier, diluent or excipient known in the art. In a preferred embodiment, this pharmaceutical composition also comprises a p53 inhibitor. In an alternative preferred embodiment this pharmaceutical composition also comprises stem cells.

In the context of this invention, a p53 inhibitor is a factor capable of inhibiting production of p53 protein or inhibiting the activity of p53 protein. p53 inhibitors are well known in the art and include MDM2 protein, fragments of the MDM2 protein and pifithrin-α.

A method of manufacturing a pharmaceutical composition is also provided. The method comprises providing a peptide or mimetic compound according to the invention and manufacturing a pharmaceutical composition comprising this peptide/mimetic compound. Where the pharmaceutical composition contains a p53 inhibitor, this is incorporated into the pharmaceutical composition during manufacture. Where the pharmaceutical composition contains stem cells, this is incorporated into the pharmaceutical composition during manufacture.

The invention also provides a method of treating a patient having a cancer, which method comprises treating the patient with this pharmaceutical composition. Where the cancer contains cells expressing wild type p53, it is preferred that the patient is treated with a pharmaceutical composition comprising a p53 inhibitor.

The pharmaceutical composition of the present invention is effective in treating cancers of various origins, including breast cancer, prostate cancer, colorectal cancer, bladder cancer, ovarian cancer, endometrial cancer, cervical cancer, head and neck cancer, stomach cancer, pancreatic cancer, esophageal cancer, small cell lung cancer, non-small cell lung cancer, malignant melanomas, neuroblastomas, leukaemias, lymphomas, sarcomas and gliomas. As discussed above, cancer cells can be identified by the method of WO 99/42821. Cancer cells are for example cells in which the ratio of the expression levels of the CDK1 and CDK4 proteins is in the range 0.6 to 1.6.

The present invention also provides a peptide or mimetic compound for use in medicine. In addition, it provides a combined preparation comprising the peptide or mimetic compound and a p53 inhibitor for simultaneous separate or sequential use in medicine.

The invention also provides the use of a peptide/mimetic compound in the manufacture of a medicament for the treatment of cancers, and the use of a peptide/mimetic compound and p53 inhibitor in the manufacture of a combined preparation for simultaneous, separate or sequential use in the treatment of cancers, including those mentioned above. Again, if the cancer contains cells that express wild type p53, it is preferred that this is treated with a combined preparation comprising a p53 inhibitor.

Cancer cells expressing wild type p53 (i.e. p53 containing no mutations) can be identified by methods known in the art. For example, wild type p53 may be identified by DNA sequencing, or by immunochemistry using antibodies specifically distinguishing between mutant p53 protein and wild type p53 protein.

In degenerative disorders the cells comprising the particular tissue cells undergo cell death at an earlier time than similar cells in a normal healthy individual. It is known from Morris et al (Morris et al. (2002) Oncogene 21, 4277) that normal CDK4 may be capable of extending the survival of non-cancerous cells. Therefore, peptides of the present invention may be of benefit in the treatment of many degenerative disorders in which cells of particular tissues die earlier than they should in the affected individual.

Therefore, the present invention also provides a method of treating a patient having a degenerative disorder, which method comprises treating the patient with the pharmaceutical composition of the present invention. It is preferred that the patient is treated with the pharmaceutical composition further comprising stem cells.

This method of treatment of a degenerative disorder may be in combination with stem cell therapy or as an adjunct to improve the efficacy of stem cell therapy. At the present time stem cell therapy is widely believed to be able to cause improvement in disorders due to inappropriately early cell death. Stem cells are normal cells which have not fully differentiated or senesced and when implanted into tissues in which cell damage has occurred are capable of proliferating to replace the dead cells.

The pharmaceutical composition of the present invention is also provided for treating degenerative disorders when the pharmaceutical composition comprises the peptide or mimetics of the present invention which are capable of stimulating the growth of non-cancerous and/or control cells. This pharmaceutical composition is effective in treating degenerative disorders including alzheimer's disease, muscular dystrophy, macular degeneration, early onset diabetes due to loss of beta cells in the pancreas, traumatic spinal cord damage, motor neuron disease and cystic fibrosis.

The present invention further provides a combined preparation comprising the peptide or mimetic compound of the present invention which is capable of stimulating the growth of non-cancerous and/or control cells and stem cells for simultaneous separate or sequential use in medicine.

The invention also provides the use of the peptide or mimetic compound of the present invention which is capable of stimulating the growth of non-cancerous and/or control cells in the manufacture of a medicament for the treatment of a degenerative disorder, The invention also provides the use of the peptide or mimetic compound of the present invention which is capable of stimulating the growth of non-cancerous and/or control cells and stem cells in the manufacture of a combined preparation for simultaneous, separate or sequential use in the treatment of a degenerative disorder.

Those skilled in the art could determine suitable administration regimens for the peptide or mimetic compound of the present invention. The precise administration regimen will depend upon the physicochemical properties of the peptide or mimetic compound.

Peptides or mimetics of the present invention may be tested by a screening method which comprises providing a peptide as defined above, or a mimetic compound capable of functionally mimicking such a peptide, followed by treating a cancer cell sample with the peptide or mimetic compound and determining the cytotoxic effect of, and/or the growth inhibiting effect of this peptide or mimetic compound on this sample. The method also involves a step of identifying a peptide or mimetic compound that is effective in the treatment of cancer as a peptide or mimetic compound that is cytotoxic to, or inhibiting to the growth of, the cancer cell sample. Optionally, a step of producing the identified peptide or mimetic compound may follow.

In a preferred embodiment, the method further comprises treating a control cell sample with the peptide or mimetic compound and determining the cytotoxic effect of, and/or the growth inhibiting effect of this peptide or mimetic compound on this sample. A peptide or mimetic compound that is effective in the treatment of cancer is a peptide or mimetic compound that more cytotoxic to, or more inhibiting to the growth of, a cancer cell sample than a control cell sample.

In a preferred embodiment, the method also involves a step of treating a control cell sample with the peptide or mimetic compound and determining whether the identified peptide or mimetic compound is non-inhibitory to the growth of a control cell sample and optionally determining whether the identified peptide or mimetic compound is stimulating to the growth of a control cell sample. A peptide or mimetic compound that is advantageous in the treatment of cancer is a peptide or mimetic compound that is non-inhibitory to the growth of a control cell sample and may also be stimulating to the growth of a control cell sample. A peptide or mimetic compound that is advantageous in the treatment of degenerative disorders is a peptide or mimetic compound that is stimulating to the growth of a control cell.

Cancer cells, control cells and non-cancerous cells have been defined above. Appropriate culture conditions for such cells are known in the art. Typically then, the step of treating a cancer cell sample and a control cell sample with the peptide or mimetic compound and determining the cytotoxic effect of, and/or the growth inhibiting effect of these, simply comprises adding the test peptide or test peptide mimetic to the culture medium. Controls are preferably included. These may include adding no test peptide/mimetic compound to samples of cells or adding a peptide/mimetic compound known to have no effect on viability.

Methods of determining whether a peptide or mimetic compound is cytotoxic or growth inhibiting to a cell sample are well known to those skilled in the art. These include inspection of treated and untreated cell samples using phase contrast microscopy, the MTT cytotoxicity assay (Roche Molecular Biochemicals, Indianapolis, Ind., USA), the propidium iodide staining assay (Do et al. Oncogene (2003) 22:1431-1444), cell death detection ELISA (Roche Molecular Biochemical, Indianapolis, Ind., USA), the caspase activity assay (Clontech, Palo Alto, Calif., USA) and the CytoTox 96 non-radioactive cytotoxicity assay (Promega, Madison, Wis., USA).

BRIEF DESCRIPTION OF FIGURES

FIGS. 1(d) and (e) show similar increase in proteomic expression of Cdk4 (d) and endogenous Cdk1 (e) in 2780 human ovarian carcinoma clone 1 D cells following exposure to ponasterone, measured by Western blotting. Clone 1D cells produced by transfection of 2780 with pvgrPINDK4 vector.

FIG. 1(f): Western blotting shows no increase in pRb105 expression following exposure of 2780 pvrgPINDK4 clone 1 D cells depicted in d) and e) following exposure to ponasterone.

FIG. 1(g) shows an alignment of linear sequences of Cdk4 (SEQ ID NO: 37), Cdk6 (SEQ ID NO: 38) and Cdk2 (SEQ ID NO: 39) identifying a duodecameric segment, amino acid residues 249-260, (boxed) unique to Cdk4.

FIGS. 1(h) and (i) show structural space filling (h) and helix-loop-helix (i) models of Cyclin dependent kinase 4 protein showing localization of externalized hydrophobic loop (bottom of (h) and enclosed in arrowed box (i)) containing the FPPRGPRPVQSV (SEQ ID NO: 21) region.

FIGS. 6 (e) and (f) shows clonogenic cell survival assays of RT112 human transitional cell bladder cancer cells following exposure to PRGPRP (SEQ ID NO: 2, Ac-Pro-Arg-Gly-Pro-Arg-ProNH2) (e) or PRRPGP (SEQ ID NO: 22, Ac-Pro-Arg-Arg-Pro-Gly-Pro-NH2) (f).

FIG. 6(g) shows sequential Western blots of RT112 human transitional cell bladder cancer cells growing in-vitro after exposure to PRGPRP (SEQ ID NO: 2) (Ac-Pro-Arg-Gly-Pro-Arg-Pro-NH2) or PRRPGP (SEQ ID NO: 22) (Ac-Pro-Arg-Arg-Pro-Gly-Pro-NH2). Peptides were introduced at day 0 and left in-situ throughout the experiment.

FIGS. 6(h) and (i) show clonogenic assays of human cancer cells exposed to the PRGPRP (SEQ ID NO: 2) motif in cyclic amphiphlic cassettes. THR53 (SEQ ID NO: 9, cyc-[PRGPRPVKLALKLALKFP]); THR53C (SEQ ID NO: 23, cyc-[FPPRRPGPVKLALKLALK], a control peptide); THR54 (SEQ ID NO: 10, cyc-[PRGPRPVALKLALKLAL]); THR79 (SEQ ID NO: 11, cyc-[PRGPRPvalklalklal]).

DETAILED DESCRIPTION OF THE INVENTION

Figure 1:
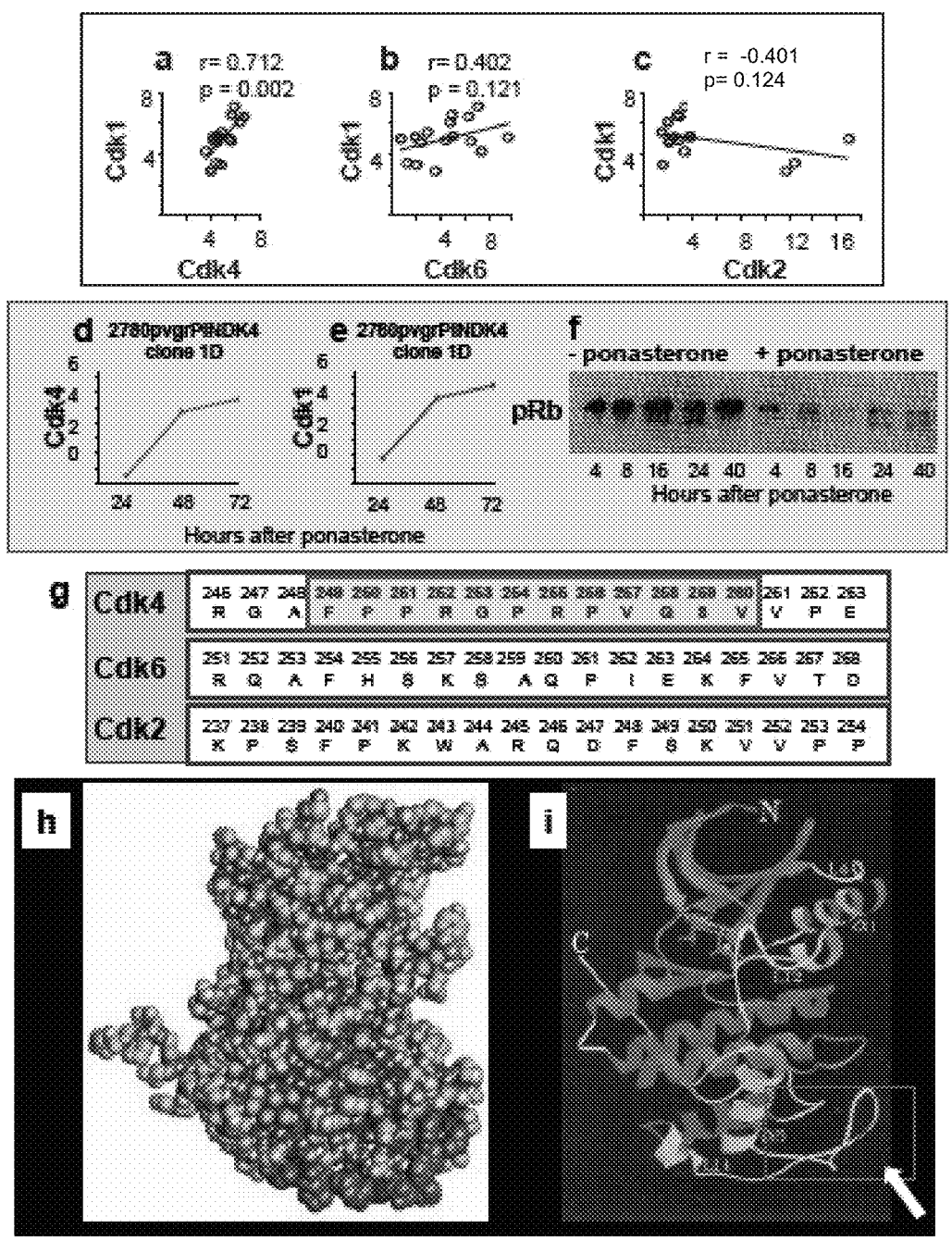
FIGS. 1 (a), (b), and (c) show relative proteomic expression by Western blotting, of Cdk4, Cdk6 and Cdk2 compared to Cdk1.

Peptides can be synthesized according to standard methods. Alternatively, they may be produced by recombinant DNA technology and gene expression technology.

When the peptide includes the Penetratin™ sequence, for example in the second aspect of the invention, the peptide may be produced by cloning DNA encoding the peptide into a Transvector™ vector (Qbiogene Inc., Carlsbad, Calif., USA), transforming an *E. coli* strain having the T7 polymerase gene with the vector and expressing the peptide by induction with IPTG (Isopropyl-β-D-thiogalactoside; Roche Molecular Biochemicals, Indianapolis, Ind., USA). Transvector™ vectors may be used to produce fusion proteins comprising the Penetratin™ sequence.

Mimetics of the peptides of the present invention may be designed and synthesized according to standard methods. Methods of modifying peptides to produce peptide mimetics are discussed in Kieber-Emmons et al. (Curr. Opin. Biotechnol. (1997) 8: 435-441) and Beeley (Trends Biotechnol. (1994) 12: 213-216).

Peptide mimetics also include "peptoids" in which one or more amino acids are replaced by the 'peptoid' fragment N(R*)CH$_2$CO, wherein R* is the side chain of the amino acid. In addition, peptide mimetics include peptides where the ends of the peptide sequence are linked through a spacer molecule to give a less flexible structure.

Non-peptide mimetics include analogues of the peptides of the invention where the various amide bonds (CONH) have been replaced with alternative bonding patterns such as C—C (carbon to carbon single bonds), C═C (carbon to carbon double bonds), C≡C (carbon to carbon triple bonds), SO$_2$NH (sulphonamides), NH.CO.NH (ureas), CO.O (esters), C(R'R")O or OC(R'R") (ethers), CH(R)CONH or CONHCH (R) (β-amino acids), NHCO (reverse peptides), wherein R is any stable substituent.

Non-peptide mimetics may also be molecules consisting of a rigid scaffold composed, for example, of aromatics, polyaromatics, heteroaromatics, cycloalkyl rings or cyclic amides, and substituents mimicking the side chain functionality found in the native peptide (e i.e. guanidine, amide, alkyl) such that the relative arrangement of the side chain functionality in the bioactive conformation of the peptide is effectively mimicked by the relative arrangement of the side chain functionality in the small drug molecule. An example of this approach may be found in Liao et al, J. Med. Chem. 1998, 41, 4767-4776. A piperazine ring is used as a template to which non-peptide ligands are attached with the aim of mimicking the side chain functionality of the original peptide. Vogt et al adopted a similar approach in J. Biol. Chem, 270 (1995), 660-664.

EXAMPLES

Example 1

Structural Studies on Cdk4

Cdk4 is co-expressed with Cdk1 in a wide range of human cancers in-vitro and malignant melanoma in the clinic but not in normal diploid fibroblasts or keratinocytes (Seabra L, Warenius H. Proteomic co-expression of cyclin-dependent kinases 1 and 4 in human cancer cells. Eur J Cancer 2007; 43: 1483-1492, see FIG. 1a). Cdk2 and Cdk6 do not show similar co-expression (FIG. 1b, 1c). Disruption of Cdk1/Cdk4 co-expression has been observed to accompany spontaneous cancer cell death in-vitro (Warenius H, Kyritsi L, Grierson I, Howarth A, et al. Spontaneous regression of human cancer cells in-vitro: Potential role of disruption of Cdk1/Cdk4 co-expression. Anticancer Res 2009).

Transfection of exogenous CDK4 in a pcDNA3 vector results in elevation of Cdk4 plus concomitant elevation of endogenous Cdk1 in RAMA 37 cells (Seabra L, Warenius H. Proteomic co-expression of cyclin-dependent kinases 1 and 4 in human cancer cells. Eur J Cancer 2007; 43: 1483-1492). In addition, activation of CDK4 transcription, in a conditionally expressing vector in 2780 human ovarian cancer cells, also caused endogenous Cdk1 elevation (FIG. 1d, 1e), which was not accompanied by pRb hyper-phosphorylation (FIG. 1f). The mechanism(s) underlying Cdk1/Cdk4 co-expression might therefore possibly involve kinase-independent Cdk4 activity. These observations plus increasing evidence of kinase-unrelated activities in cyclin-dependent and other kinases (above) and the relative importance of Cdk4 compared to Cdk2 and Cdk6 in carcinogenesis, prompted a search for a functional site of kinase-independent activity specific to Cdk4 but not Cdk2 or Cdk6. Binding sites for proteins intrinsic to Cdk4 kinase activity such as pRb, cyclin D, pINK4 and the ATP-binding kinase activity site, all lie predominantly within the N'-terminal 2/3 of the Cdk4 protein. Structural studies of the whole Cdk4, Cdk6 and Cdk2 molecules were therefore carried out to search for a kinase-independent functional site within the C'-terminal domain of Cdk4, not shared by Cdk6 or Cdk2.

In the absence of known publicly available crystal structures for CDK4, the considerable sequence homology across the CDK protein family was used to produce a comparative model. Related sequences and important regions within the CDK4 sequence were identified, a model of CDK4 based on experimentally determined structures of CDK6 was built and CDK2 and regions in the CDK4 model that might provide support for a kinase-unrelated binding site were sought.

The sequence identity (percentage of identical residues) and sequence similarity (percentage of similar residues) in the two sequences to the *Homo sapiens* CDK4 sequence was determined. Despite considerable similarity, the alignment of the additional non-mammalian CDK4 sequences provided interesting results. The first half of the sequence, corresponding to the first domain and responsible for the majority of CDK4 function, is, as would be expected, well conserved. The latter third of the sequence, however, showed considerable variability. In particular, our attention was drawn to the FPPRGPRPVQS (SEQ ID NO: 28) sequence unique to Cdk4 which showed little or no conservation beyond mammalian species.

Alignment of the sequences of CDK4, 6, and 2 showed considerable conservation between all three Cdks as expected. The 12mer segment previously identified in the CDK4 alignment, however, exhibited very little sequence homology with the same aligned fragments in CDK6 and CDK2 (FIG. 1g), showed differences in overall charge and hydrophobicity and could potentially provide a protein binding site. A search for similar sequences in the Swiss-Prot and TrEMBL databases using the fragment sequence "FPPRG-PRPVQSV" (SEQ ID NO: 21) was therefore undertaken. Apart from mammalian CDK4 sequences, the search returned three types of protein, the most promising of which were the Ras-GTPase-activating proteins. A search for these in the PDB, however, proved unsuccessful. In the ProDom database the fragment sequence did not correspond to any recognized domain, although the Ras binding domain is currently unidentified. A further search performed using all residues within 10 Å of the fragment sequence, however, proved negative. Thus the putative protein-binding site in CDK4 showed no identifiable similarity with other known sequences.

The high sequence homology of the CDK6 sequence to CDK4 would normally make it unnecessary to consider CDK2 as a template. However, the resolutions of the CDK6 structures are generally not good (>2.5 Å) and contain bound proteins which may distort their structures. To supplement the collection of CDK6 structures, two CDK2 structures were chosen as suitable templates; both have high resolutions. 1 HCK is an apo structure and 1 GII has the ATP binding region mutated to that of CDK4, thus providing the only direct structural evidence for CDK4. The chosen template structures were checked for errors and problems that might affect the structure building process using WHAT-CHECK. Although the structures obtained were sub-optimal, giving inherently unreliable models with missing segments, mainly localized to domain 1, the model could provide reliable information on the tertiary structure, the position of the amino-acid residues within the structure, and whether those residues are buried or solvent accessible.

The results of 5 different homology models are summarized in Table I. A model using the CDK6 structure 1 BLX as template (model 1) was found to be the most reliable overall. The majority of the errors in the five models arise from the modelling of the loop regions in domain 1. This is unsurprising, as it is these loops that are involved in protein-protein interactions in the crystal structures and as such show considerable variability. The loop containing the previously identified 12mer (in red in the space filling model. FIG. 1*h*) is solvent accessible in all models and varies only slightly in conformation.

The structure of CDK4 model 1 closely resembles Cdk6 and is shown in FIG. 1 *i*), focusing specifically on the 12mer sequence identified earlier. This solvent-accessible sequence is very hydrophobic, is situated in domain 2 at the furthest point away from domain 1 and differs in electrostatic charge from Cdk2 and Cdk6, containing only two Arg residues as compared to His, Lys and Glu in Cdk6 or Lys and Asp in Cdk2. The greater predominance of small residues, Gly and Pro, in the CDK4 sequence compared to the CDK6 sequence results in a much flatter surface potentially providing better surface contact for a protein partner. Additionally, unlike both CDK6 and CDK2, the charged residues in the Cdk4 sequence, both arginines, are situated at the center of the fragment. The rest is distinctly not charged.

The amino acid sequences used in this work were obtained from the Swiss-Prot and TrEMBL databases, maintained at the Expasy molecular biology server (ca.expasy.org). The sequence similarity searches were performed using BLAST (1), maintained by the Swiss Institute for Biology (SIB), using default parameters unless otherwise stated. The sequences for potential templates were obtained from the PDB via a Blast search. Global multiple sequence alignments were performed using the program ClustalX (2). Secondary structure alignments were performed using Swiss PDB-viewer v3.7 (3).

Modelling Work

The x-ray crystal structures of CDK6 and CDK2 were obtained from the PDB. The suitability of the structures as templates was assessed by the program WHAT-CHECK (4). The program JACKAL was used to build the homology model. The program Profix, a utility program distributed with JACKAL, was used to replace those residues and atoms missing from the structures. The models were constructed as follows:

1. Using the global multiple alignment, corrected for secondary structure, the program mutates non-conserved residues while retaining the original backbone conformation. The mutated residues are subjected to energy minimization to remove atom clashes. The minimization is performed in torsion angle space, using the fast torsion angle minimizer implemented in JACKAL. The energy function uses the CHARMM22 all atom force field (6) Insertions and deletions are then performed, with the bonds closed using a random tweak method. The results are again minimized.
2. The secondary structure is assigned using a DSSP-like routine (7).
3. Prediction of the identified loop regions follows. The prediction is performed as follows: a) First, the original backbone segment is deleted and replaced by a new segment that is made by generating a large number of random backbone conformations, which are then closed using a random tweak method, b) the closed conformers are subjected to energy minimization using the fast torsion angle minimizer, c) the side chains are then modelled using a large rotamer library of 3222 rotamers in 10° bins and subjected to further minimization, d) the best candidate, the conformer with the lowest energy, is retained, and a further round of conformation sampling is performed about the new conformation, e) the final structure is subjected once again to energy minimization.
4. The secondary structure elements are then refined by again sampling through a backbone rotamer library, but with the original rotamer retained in the sampling. To retain the hydrogen-bonding network of the existing secondary structure, a large energy penalty is incurred by any conformation that breaks an existing hydrogen bond (hydrogen bonds are defined as in DSSP). The lowest energy conformation is retained. The side chains are then built in a similar way.
5. The final model is minimized using the torsion angle minimizer
6. After the construction of the model, the model is subjected to 500 steps of steepest descent full energy minimization using AMBER, with the parm96 force field (8). The polar hydrogen atoms were added by WHATIF (9) after optimizing the hydrogen-bond network.
7. Steps 1-6 were repeated until no further improvement in the model was obtained.
8. At points it was also necessary to manually tweak the structures. This was performed through the Swiss PDB-viewer. The final models were assessed for accuracy and quality by the programs WHAT-CHECK and Swiss PDB-viewer. The threading energy given by Swiss PDB-viewer is based on the potential of mean force developed by Sippl et al (10). The molecular mechanics energy is calculated using the GROMACS96 force field (11), and is also implemented in Swiss PDB-viewer.

Example 2

Testing the Efficacy of Peptides Derived from FPPRGPRPVQSV (SEQ ID NO:21)

Proteomic expression levels of Cdk1 and Cdk4 appear to go up and down together from experiment to experiment (Warenius H, Howarth A, Seabra L, Kyritsi L, Dormer R, Anandappa S, and Thomas C. Dynamic heterogeneity of proteomic expression in human cancer cells does not affect Cdk1/Cdk4 co-expression. J Exp Ther Oncol, 7: 237-254, 2008). This observation along with evidence that Cdk4 overexpression following transfection causes concomitant increase in Cdk1 expression (Seabra L, Warenius H. Proteomic co-expression of cyclin-dependent kinases 1 and 4 in human cancer cells. Eur J Cancer 2007; 43: 1483-1492) and disruption of Cdk1/Cdk4 co-expression can accompany spontaneous human cancer cell death 20, suggested that the FPPRGPRPVQSV (SEQ ID NO: 21) region of Cdk4 might act as the agonistic component of a feedback loop controlling Cdk1 and Cdk4 co-expression. Possible cancer cell stabilization by a Cdk1/Cdk4 co-expression feedback mechanism might be vulnerable to competitive inhibition. Human cancer cells were therefore exposed to peptide fragments of varying length derived from the FPPRGPRPVQSV sequence (SEQ ID NO: 21) and the effects on cell growth and relative Cdk1/Cdk4 levels monitored.

The central hexamer PRGPRP (SEQ ID NO: 2) of FPPRGPRPVQS (SEQ ID NO: 28) was found to be particularly biologically active. Complete cell death of MGHU-1 Human transitional bladder cancer cells was observed morphologi-

TABLE I

Quality and accuracy scores for the built models.

Figure 2:
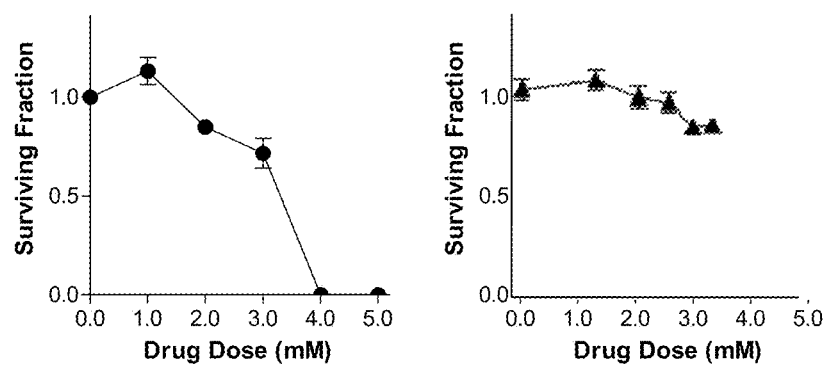
FIG. 2 shows the results of a clonogenic assay showing the effect of PRGPRP (SEQ ID NO: 2) on RT112 Bladder cancer cells (left panel) or H460 Non-small cell lung cancer cells (right panel).

| | MODEL | | | | |
| --- | --- | --- | --- | --- | --- |
| | Model 1 | Model 2 | Model 3 | Model 4 | Model 5 |
| Template | 1BLX (CDK6) | 1G3N (CDK6) | Base template 1BLX, Variable regions differing by more than 2.0 Å rmsd. modelied from 1G3N, 1BI6, 1BI7 and 1JOW (all CDK6) | Base template 1BLX, Variable regions differing by more than 2.0 Å rmsd. modelied from 1HCL (CDK2) | Base template 1BLX, Variable regions differing by more than 2.0 Å rmsd. modelied from 1GII (CDK2) |
| Threading score | 165.6 | 156.2 | 151.0 | 128.6 | 99.7 |
| Molecular mechanics energy (kJ mol$^{-1}$) | −12203.3 | −12526.1 | −12182.5 | −11900.3 | −11795.5 |
| RMS deviation from 1BLX (in Å) | 0.48 | 0.88 | 0.62 | 0.67 | 0.65 |
| Structure Z-scores, positive is better than average | | | | | |
| $2^{nd}$ generation packing quality | −1.093 | −0.868 | −0.964 | −1.090 | −1.228 |
| Ramachandran plot appearance | −2.573 | −3.374 | −2.837 | −2.965 | −3.104 |
| Z-1/Z-2 rotamer quality | −1.148 | −1.470 | −1.340 | −0.955 | −0.968 |
| Backbone conformation | −6.465 | −5.201 | −5.637 | −7.016 | −7.564 |
| RMS Z-scores, should be close to 1 | | | | | |
| Bond lengths | 0.655 | 0.645 | 0.652 | 0.657 | 0.666 |
| Bond angles | 1.187 | 1.176 | 1.183 | 1.168 | 1.181 |
| Omega angle restraints | 1.354 | 1.159 | 1.413 | 1.478 | 1.386 |
| Side chain planarity | 1.606 | 1.667 | 1.494 | 1.277 | 1.292 |
| Improper dihedral distribution | 0.883 | 0.882 | 0.907 | 0.879 | 0.865 |
| Inside/Outside distribution | 1.019 | 1.036 | 1.025 | 1.043 | 1.051 | cally in-vitro 25 days after exposure to a 5.0 mM concentration of commercially prepared end-capped Ac-Pro-Arg-Gly-Pro-Arg-Pro-NH2 (SEQ ID NO:2; FIG. 2a). Normal diploid human fibroblasts in short term culture were unaffected (FIG. 2b). Cancer cell lethality was confirmed by clonogenic assays on RT112 human bladder cancer cells (FIG. 2a, FIG. 6e), noting that PRGPRP (SEQ ID NO: 2) has no effect on H460 non-small cell lung cancer (FIG. 2b). However, PRGPRP (SEQ ID NO: 2) is only effective at killing RT112 bladder cancer cells at a concentration of 5.0 mM. Because of concern that such high peptide doses might cause artefactual, non-specific effects, structure/function studies were carried out. Ac-Pro-<u>Arg-Arg</u>-Pro-Gly-Pro-NH2 (SEQ ID NO: 22) was inactive against RT112 (FIG. 6f) which demonstrated that the relative positions of the two arginines were critical to cancer cell killing.

Example 3

Linear Peptides Comprising an Amphiphilic Sequence

PRGPRP (SEQ ID NO: 2) according to WO2005/123760 was found to exhibit weak specific activity. 5 mM was required to produce 100% lethality in in vitro experiments on RT 112 (FIG. 2a) or MGHU-1 human bladder cancer cells. This limits the applicability of PRGPRP (SEQ ID NO: 2) to therapy even though it has selected killing activity in human cancer cells but not normal human fibroblasts.

In order to aim to improve the properties of PRGPRP (SEQ ID NO: 2), a longer peptide was sequenced which included an amphiphilic region attached to the PRGPRP (SEQ ID NO: 2) by a valine spacer to provide adequate spacing between the arginine and the lysine. The result was a linear peptide with the following sequence Ac-PRGPRPVKLALKLALKAL-NH₂. This peptide was given the code THR51 (SEQ ID NO: 29).

A control for THR51 was termed THR51C (SEQ ID NO: 30) in which one arginine was switched with a glycine to provide the sequence Ac-PRRPGPVKLALKLALKAL-NH₂. This control would be expected to have lost its specific anti-cancer killing effect because of this switch.

The effect of these peptides was tested on both human fibroblasts and H460 human non-small cell low cancer cells at doses in the range 12.5 to 100 µM. The peptides were tested in vitro by exposure to 100 H460 human non-small cell lung cancer cells, or short term cultures of normal human diploid fibroblasts, in 200 ul of Ham's F12 tissue culture medium supplemented with 10% FCS. Cells were set up in 100 ul on day 0 and 24 hours later a further 100 ul of the same medium containing ×2 the appropriate concentration of peptide over a range of 12.5-100 uM was added. The cells were then incubated at 37° C., 5% CO₂ in an humidified incubator for 2-4 weeks.

Cell viability was measured by an MTS assay (CellTiter 96$^R$ Non-Radioactive Cell Proliferation Assay. Promega Corporation, 2800 Woods Hollow Road, Madison Wis. 53711-5399 USA). The original form of this assay was described by Mosmann (J. Immunol. Meth. 65; 55-63. 1983) and gives a colorometric reading whose intensity depends on the conversion, by viable cells, of a tetrazolium salt into a coloured formazan which is easily quantified by colorimetric reading of a 96 well assay plate.

Figure 3:
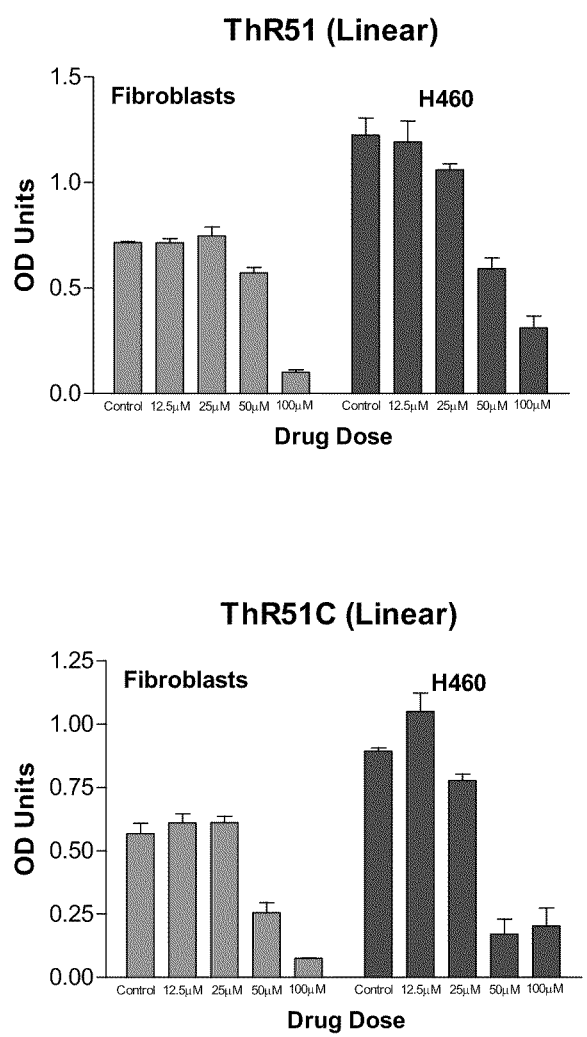
FIG. 3 shows how cell viability changes in response to different dosages of a linear peptide outside the scope of the invention.

The results are shown in FIG. 3. Although there is an improvement in cancer cell killing over PRGPRP (SEQ ID NO: 2), specific anti-cancer activity was lost. Fibroblasts were found to be equally as well killed by THR51 (SEQ ID NO: 29) as cancer cells. In addition, non-specific killing by THR51C control (SEQ ID NO: 30) was equally seen. The improvement in cancer cell killing could be attributed to improved cell uptake.

The inventors have also found that attachment to penetratin produced PRGPRP (SEQ ID NO: 2) killing at lower doses but this was non-specific because normal fibroblasts were equally killed in a similar manner to that seen with THR51 (above).

Example 4

Cyclisation Alone does not Improve Efficacy

The inventors have discovered that simply including PRGPRP (SEQ ID NO:2) within cyclical peptides alone does not improve their efficacy. Table 2 lists cyclic peptides including the PRGPRP (SEQ ID NO:2) sequence which have no effect on RT112 bladder cancer cells at a concentration of 100 µM.

TABLE 2

| | Cell Killing | |
|---|---|---|
| Cyclic Peptide Sequence | RT112 | Fibro-blasts |
| Cyc-[GGGGGGPRGPRPGGGGGG] (SEQ ID NO: 31) | - - - | - - - |
| Cyc-[AAAGGGPRGPRPGGGAAA] (SEQ ID NO: 32) | - - - | - - - |
| Cyc-[GGGGPRGPRPGGGGPRGPRPVPRGPRPV] (SEQ ID NO: 33) | - - - | - - - |
| Cyc-[AAGPGGPRGPRPGGPGAA] (SEQ ID NO: 34) | - - - | - - - |

[- - - = No cell killing].

Although WO2005/123760 A3 disclosed that the cyclic peptide sequence cyc-[PRGPRPVPRGPRPVPRGPRPV] (SEQ ID NO: 35) caused morphological changes in MGHU1 cells this cyclic peptide did not kill MGHU1 cells, although it did markedly stimulate normal fibroblasts. The normal cell stimulating effect of these compounds and the cancer cell killing effects may thus reflect separate activities of PRGPRP-containing cyclic peptides.

In addition to offering a degree of protection against peptidase attack, cyclisation of proteins is also understood to facilitate cell uptake. The latter could improve the specific activity per weight of a given peptides by delivering a greater proportion of the extracellular peptide to the intracellular target.

Example 5

Improvement Provided by Use of Cyclic Peptides Comprising Amphiphilic Sequence

It can be seen from the above examples that the use of either an amphiphilic peptide sequence or a cyclic peptide alone was not sufficient to improve the potency of PRGPRP (SEQ ID NO: 2) to the desired level.

Combining cyclisation with an amphiphilic component provides PRGPRP (SEQ ID NO: 2)-containing molecules of greatly improved cell killing ability.

Figure 4:
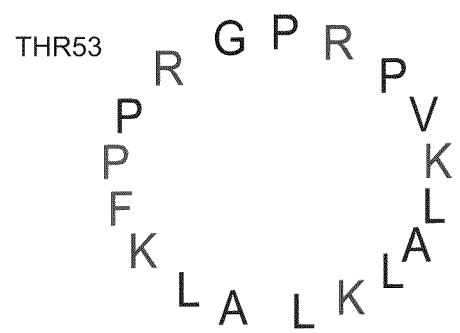
FIG. 4 shows the structure of a peptide according to the invention (SEQ ID NO: 9, THR 53).

The first experiments were carried out on cyc-[PRGPRPVKLALKLALKFP] (THR 53, (SEQ ID NO: 9)), see FIG. 4. Whilst the 96 well assays described in Example 3 are suitable for initial screening of small amounts of peptide material the long incubation periods in dense culture do themselves compromise cell viability to some extent. In addition the MTS assay can show comparative cell killing but is less effective with regards to absolute cell killing. In clonogenic assays, (previously described by Warenius et al Br J Cancer (2000) 83(8), 1048-1059) single cell suspensions of 100 cells are plated in plentiful volumes of 2 ml of Ham's F12 tissue culture medium supplemented with 10% FCS and incubated for 15, 20 or 25 days. A high percentage of the plated cells (40-60% in the case of H460) go through repeated doublings to yield colonies of 200 or more cells which can be easily visualized by the naked eye and counted under a low power lens when stained by giemsa stain.

Figure 5:
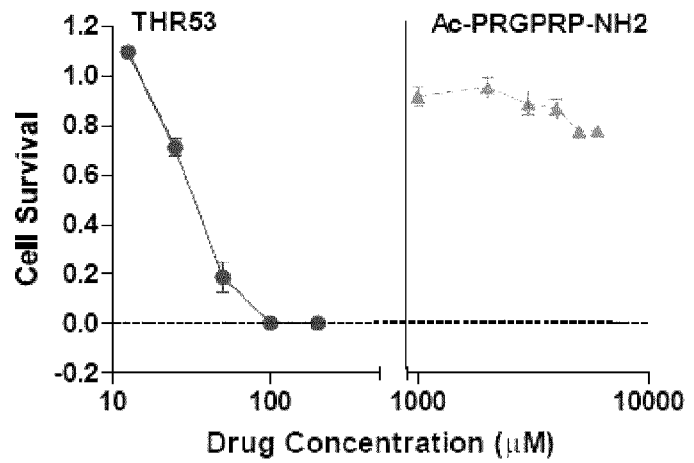
FIG. 5 shows the efficacy of a cyclic peptide according to the invention (SEQ ID NO: 9, THR 53) in a clonogenic assay.
Figure 5:
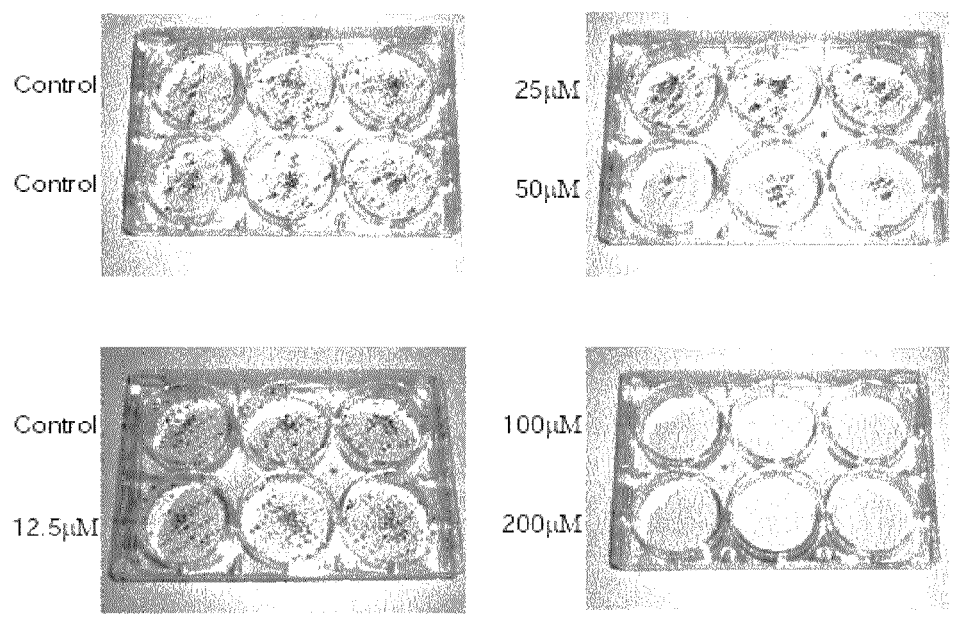

The efficacy of THR53 was compared to Ac-PRGPRP-NH$_2$ (SEQ ID NO: 2) using a clonogenic assay. The results are shown in FIG. 5. This Figure shows that H460 human non-small cell low cancer cell survival is significantly decreased when drug concentrations increase from 10 to 100 µM using THR53. In contrast, the linear Ac-PRGPRP-NH$_2$ (SEQ ID NO: 2) is found to have limited effect on cell survival even at 1 to 10 mM concentration.

FIG. 5 further contains a picture of one of the 6 well plates used to demonstrate the efficacy of THR53 showing that at a concentration of 100 uM no colonies at all are visible, indicating a 100% lethality of THR53 on H460 non-small cell lung cancer cells under these conditions.

Figure 6:
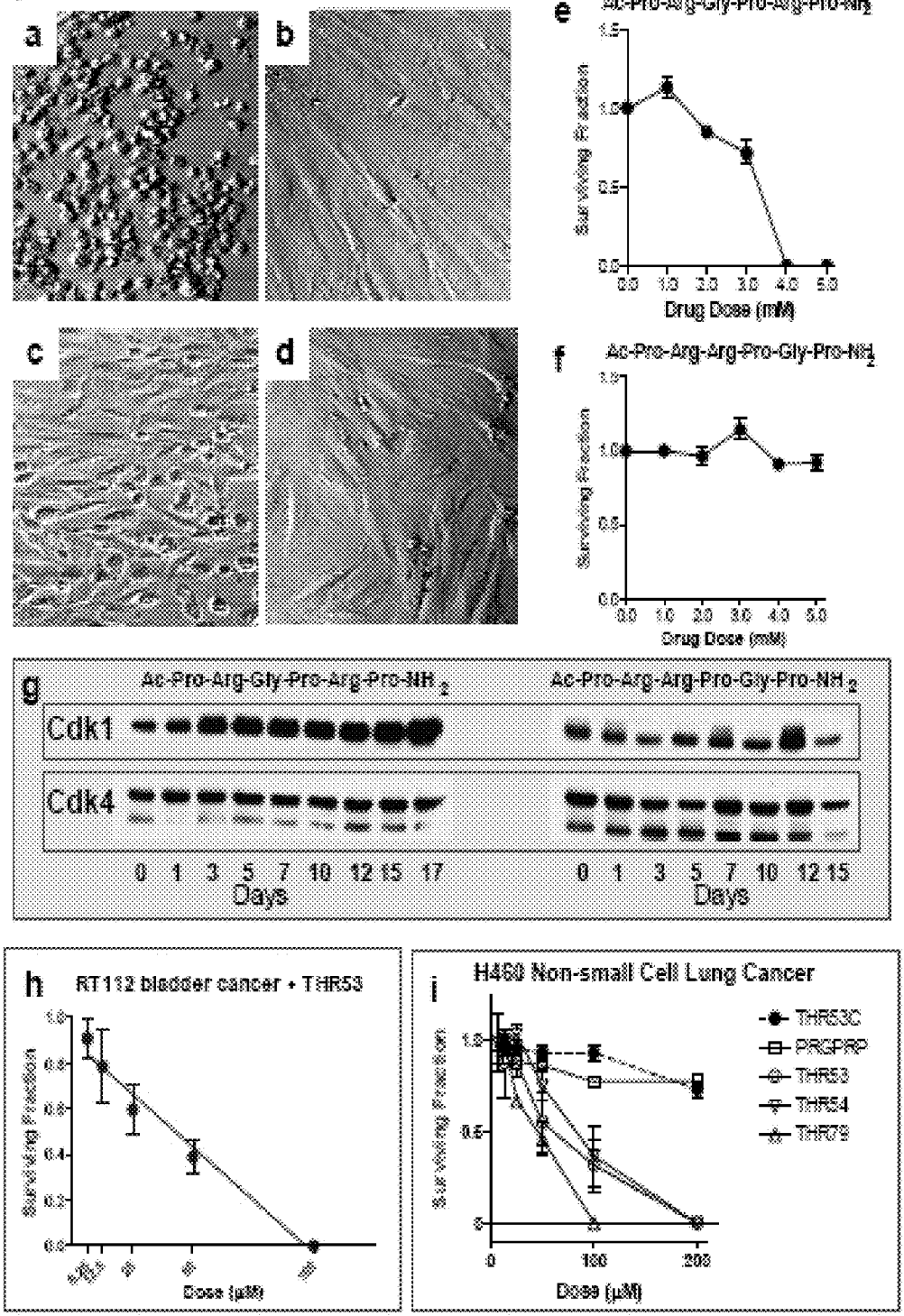
FIGS. 6 (a), (b), (c) and (d) show photomicrographs illustrating typical in-vitro morphological appearances of MGHU-1 human bladder cancer cells (a, c) and normal human fibroblasts (b, d) without (c, d) and with (a, b) exposure to 5.0 mM PRGPRP ((SEQ ID NO: 2, Ac-Pro-Arg-Gly-Pro-Arg-Pro-NH2). Magnification ×40.

The effectiveness of cyclic peptides comprising amphiphilic sequences is further illustrated in FIGS. 6h and 6i, showing the results of a clonogenic assay using the peptides THR53 cyc-[PRGPRPVKLALKLALKFP] (SEQ ID NO: 9); THR53C, cyc-[FPPRRPGPVKLALKLALK] (a control peptide, SEQ ID NO: 23); THR54 (SEQ ID NO: 10, cyc-[PRGPRPVALKLALKLAL]); THR79 (SEQ ID NO: 11, cyc-[PRGPRPvalklalklal]). Upper case=L amino acids, lower case=D-amino acids. These molecules all contain a common PRGPRP (SEQ ID NO: 2) warhead (with the exception of the control, THR53C).

The use of such amphiphilic cyclic peptides led to increased cancer cell killing at much lower concentrations (50 µM-200 µM) at shorter times of 10-15 days after peptide exposure. The previously observed, arginine-related, structure function relationship was retained in the cyclic amphiphilic compounds (THR53C, FIG. 6i).

Figure 7:
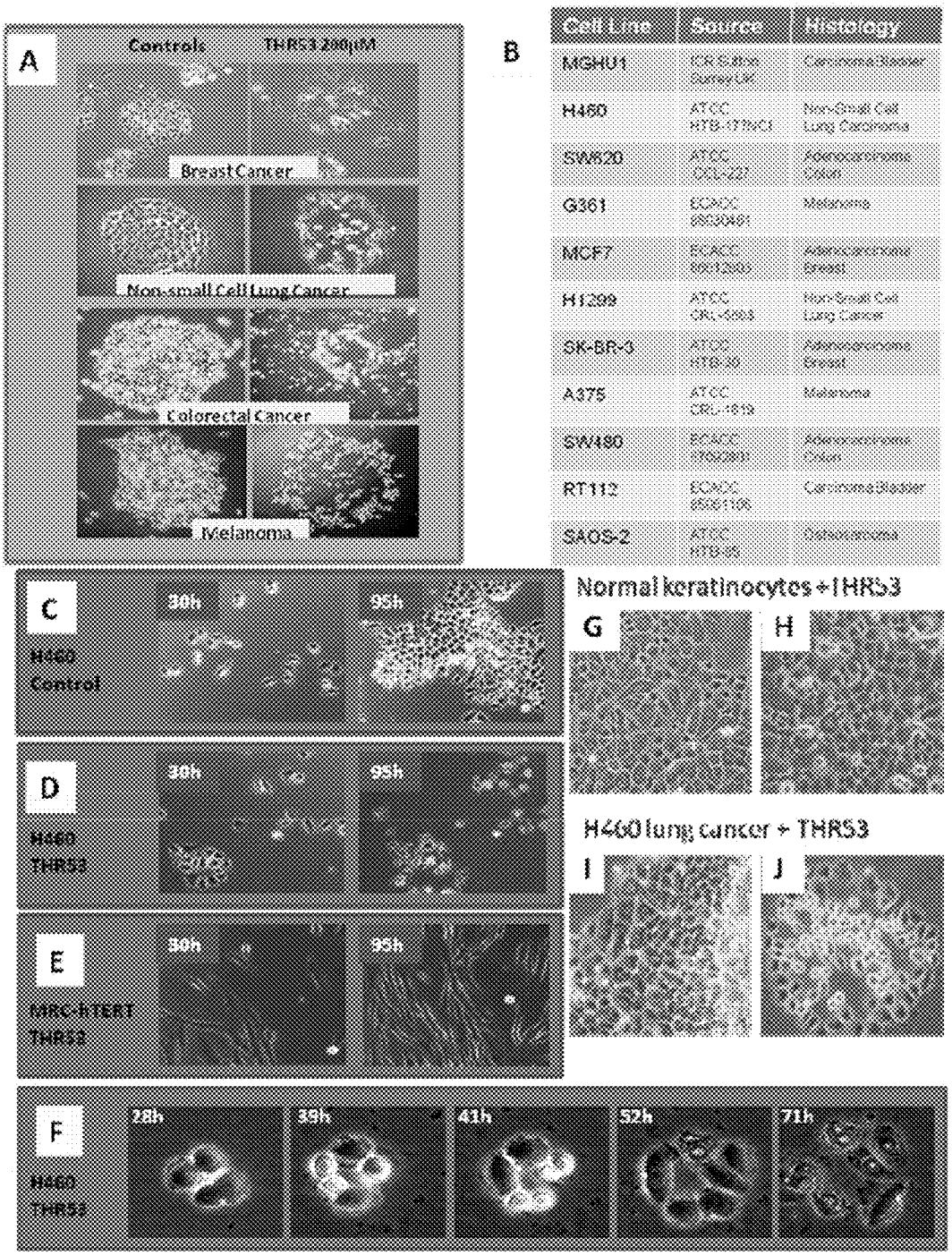
FIG. 7(a) shows photomicrographs having typical appearances of in-vitro cultures of breast cancer, non-small cell lung cancer, colorectal cancer and melanoma treated with 200 µM THR53 as compared to untreated controls. Magnification ×10.
FIG. 7(b) shows designation, source and histology of 11 human in-vitro cancer cell lines showing complete response to 200 µM THR53 (SEQ ID NO: 9).
FIGS. 7(c), (d) and (e) show time lapse photomicrographs of H460 human non-small cell lung cancer cells and MRC-hTERT immortalized normal human fibroblasts growing in tissue culture following exposure to 200 µM THR53 (SEQ ID NO: 9) (d, e) and untreated control H460 cells (c). Magnification ×10.
FIG. 7(f) shows detailed time-lapse photomicrographs of H460 human non-small cell lung cancer cells growing in-vitro following exposure to 200 µM THR53 (SEQ ID NO: 9). Morphological appearances of cell death are not those of apoptosis. Magnification ×40.
FIGS. 7(g), (h), (i,) and (j) show established cultures of H460 human non-small cell lung cancer cells (i, j) and normal diploid human keratinocytes (g, h) in the presence and absence of THR53. $10^4$ tumor or keratinocyte cells were plated in 2.5 cm diameter tissue culture wells and 5 days later vehicle (g, i) or 200 µM THR53 (SEQ ID NO: 9) (h, j) were added. Further incubation was carried out for 7 days.

Progressive increase in Cdk1 compared to Cdk4 over 15 days seen in RT112 cells killed by PRGPRP (SEQ ID NO: 2) which was not seen with PRRPGP (SEQ ID NO: 22) (FIG. 6g), and this is consistent with a hypothesis that failure to maintain Cdk1/Cdk4 co-expression should negatively influence cancer cell survival. In a clinical context this might provide a biomarker of therapeutic efficacy. Eleven human cancer cell lines covering a wide range of histologies (FIG. 7b) have all exhibited similar early morphological changes at 5 days (FIG. 7a) followed by complete lethality in clonogenic assays at 15 days after exposure to the same dose of 200 µM THR53. Such a homogeneous therapeutic response is in marked contrast to the wide range of variability in dose response of different cancer cell lines seen with conventional chemotherapeutic agents[24]. Cancer cells both underwent successful mitosis and died (FIG. 3f) or died in interphase (FIG. 7d). There were no features of apoptosis. MRC-hTERT fibroblasts (FIG. 7c) and short term cultures of normal diploid human keratinocytes (FIG. 3h) were not killed by 200 µM THR53.

Without being bound by theory, it is understood that incorporating PRGPRP (SEQ ID NO: 2) in a cyclic amphiphilic cassette probably increases its cancer cell-specific killing ability because of increased stability due to resistance to protease attack and increased cell uptake as the result of the amphiphilic sequence.

Example 6

Effect of Amino Acid Stereochemistry

It has also been discovered that the stereochemistry of the amino acids in the peptide sequence is relevant to efficacy. Analogues of THR54 (SEQ ID NO: 10) in which certain L-amino-acids have been replaced with D-amino-acids were prepared.

These are: THR75 (SEQ ID NO: 24, cyc-[PRGPRPValklalklal]); THR77 (SEQ ID NO: 25, cyc-[PRGPRPValklaIklaL]); THR78 (SEQ ID NO: 26, cyc-[PRGPRPVAlklaIklaL]); THR79 (SEQ ID NO: 11 cyc-[PRGPRPvalklalklal]). Upper case denotes the L isomer of the amino acids and lower case denotes the D isomer.

Figure 8:
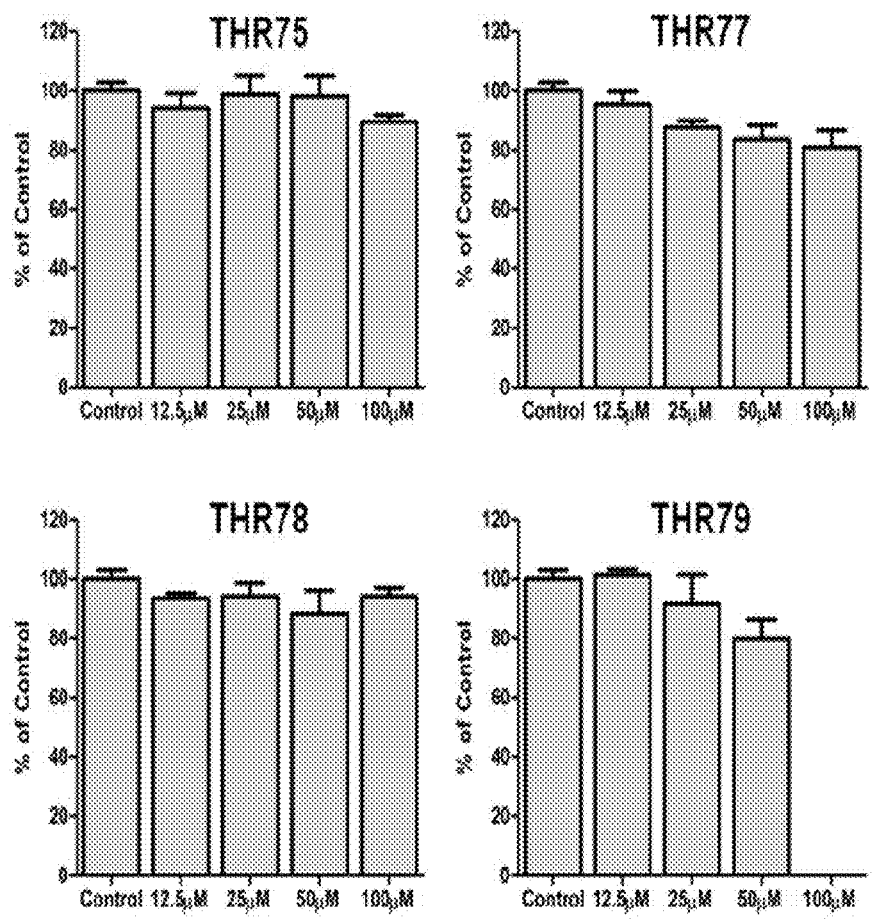
FIG. 8 shows the effect of the amino acid stereochemistry of the peptides on cancer cell-killing activity. The peptides used were: THR75 (SEQ ID NO: 24, cyc-[PRGPRPValklalklal]); THR77 (SEQ ID NO: 25, cyc-[PRGPRPValklalklaL]); THR78 (SEQ ID NO: 26, cyc-[PRGPRPValklalklaL]; THR79 (SEQ ID NO: 11 cyc-[PRGPRPvalklalklal]). Upper case denotes the L isomer of the amino acids and lower case denotes the D isomer.

Despite the fact that THR54 comprised of L-amino-acids is active, only one of the D-amino-acid substituted versions of THR54 showed cancer cell-killing properties. This was THR79 in which was approximately 2-4 times as active as THR54. THR79 had a D-valine instead of an L-valine. Changing the L-amino-acid sequence ALKLALKLAL (SEQ ID NO: 7) for the D-amino-acid sequence alklalklal as in THR 75 was sufficient to remove the activity of PRGPRP at 100 uM concentration, but also changing the L-valine to D valine restored/improved activity (see FIG. 8).

The invention claimed is:

1. A cyclic peptide which comprises:
   (i) a CDK4 peptide region; and
   (ii) a cell-penetrating region;
   wherein the CDK4 peptide region comprises the amino acid sequence $P^1R^1x^1y^1R^2P^2V$ (SEQ ID NO: 1), in which $P^1$ and $P^2$ are each proline, $R^1$ and $R^2$ are each arginine and each of $x^1$ and $y^1$ are either a linker or proline, wherein if $x^1$ is a linker then $y^1$ is proline or if $x^1$ is proline then $y^1$ is a linker, or wherein $x^1$ and $y^1$ when taken together form a linker, and wherein V may be present or absent; wherein each amino acid is the L stereoisomer or wherein the valine residue of the amino acid sequence $P^1R^1x^1y^1R^2P^2V$ (SEQ ID NO: 1) of the CDK4 peptide region is the D stereoisomer and all other amino acids in the cyclic peptide are the L stereoisomer; and
   wherein the cell-penetrating region is capable of enhancing the uptake of the cyclic peptide or a part thereof into cancer cells and comprises an amphiphilic amino acid sequence; and wherein the cyclic peptide or a part thereof is cytotoxic to and/or inhibiting to the growth of a cancer cell.

2. A cyclic peptide according to claim 1 wherein the cell-penetrating region is capable of enhancing the uptake of the CDK4 peptide region.

3. A peptide according to claim 1 wherein the linker comprises $C_1$ to $C_4$ hydrocarbylene or an amino acid.

4. A peptide according to claim 1, wherein the linker is glycine.

5. A peptide according to claim 4 wherein $x^1$ is glycine and $y^1$ is proline.

6. A peptide according to claim 1, wherein the amphiphilic amino acid sequence is 9 or 10 amino acids in length.

7. A peptide according to claim 1, wherein the amphiphilic amino acid sequence comprises ALKLALK (SEQ ID NO: 5).

8. A peptide according to claim 1, wherein the amphiphilic amino acid sequence comprises ALKLALKLAL (SEQ ID NO: 7).

9. A peptide according to claim 1, wherein the amphiphilic amino acid sequence is 9 amino acids in length, and wherein the cyclic peptide further comprises a dipeptide spacer between the CDK4 peptide region and the cell-penetrating region.

10. A peptide according to claim 9, wherein the amphiphilic amino acid sequence comprises KLALKLALK (SEQ ID NO: 8).

11. A peptide according to claim 9 wherein the dipeptide spacer is FP, such that the CDK4 peptide and the dipeptide spacer together have the sequence $FPP^1R^1x^1y^1R^2P^2V$ (SEQ ID NO:46).

12. A peptide according to claim 1, wherein the amphiphilic amino acid sequence comprises ALRLALRLAL (SEQ ID NO:41).

13. A peptide according to claim 4 in which a glycine or arginine residue in the amino acid sequence $P^1R^1x^1y^1R^2P^2V$ (SEQ ID NO:1) is methylated on the backbone amide nitrogen.

14. A peptide according to claim 13 wherein $R^1$ or $R^2$ is methylated on the backbone amide nitrogen.

15. A peptide according to claim 13 wherein $x^1$ is glycine which is methylated on the backbone amide nitrogen.

16. A peptide according to claim 1, wherein each amino acid is the L stereoisomer.

17. A peptide according to claim 1, wherein the valine residue of the amino acid sequence $P^1R^1x^1y^1R^2P^2V$ of the CDK4 peptide region is the D stereoisomer.

18. A peptide according to claim 1 which is selected from the group consisting of:

```
cyc-[PRGPRPVALKLALKLAL], cyc-[P(N-Me-Arg)GPRPVALKLALKLAL], cyc-[PR(N-Me-Gly)PRPVALKLALKLAL], cyc-[PRGP(N-Me-Arg)PVALKLALKLAL], cyc-[PRGPRPVALRLALRLAL], cyc-[PRGPRPALKLALKLAL];
and cyc-[PRGPRPVKLALKLALKFP].
```

19. A cyclic peptide which comprises
   (i) a CDK4 peptide region; and
   (ii) a cell-penetrating region;
   wherein the CDK4 peptide region comprises the amino acid sequence FXXRZXRY (SEQ ID NO: 19), in which F is phenylalanine, R is arginine, Z is a linker, X and Y are proline or threonine, Y may be present or absent and at least one of X and/or Y is proline; and residues 1 and 2 of SEQ ID NO:19 may both be present or both be absent; wherein each amino acid is the L stereoisomer; and wherein the cell-penetrating region comprises a moiety capable of enhancing the uptake of the CDK4 peptide region into cancer cells and wherein the cell-penetrating region is an amphiphilic region; and wherein the cyclic peptide is cytotoxic to and/or inhibiting to the growth of a cancer cell.

20. A peptide according to claim 19, wherein Y is present in the CDK4 peptide region.

21. A peptide according to claim 19, wherein X and Y are proline.

22. A peptide according to claim 19, wherein the linker comprises $C_1$ to $C_4$ hydrocarbylene or a non-polar amino acid.

23. A peptide according to claim 19, wherein the linker is glycine.

24. A peptide according to claim 19, which further comprises V attached to the C terminal end of the CDK4 peptide region.

25. A peptide according to claim 19, wherein the cell-penetrating region comprises a peptide.

26. A peptide according to claim 19 wherein the amphiphilic region comprises KLALKLALK (SEQ ID NO: 8).

27. A peptide according to claim 19, wherein the peptide is non-inhibitory to a non-cancerous cell and/or a control cell.

28. A pharmaceutical composition comprising the peptide of claim 1, and a pharmaceutical carrier, diluent or excipient.

29. A pharmaceutical composition according to claim 28, further comprising a p53 inhibitor.

30. A pharmaceutical composition according to claim 29, wherein said p53 inhibitor is pifithrin-α.

31. A method of manufacturing a pharmaceutical composition, comprising:
   a) providing a peptide as defined in claim 1;
   b) optionally providing a p53 inhibitor;
   c) manufacturing a pharmaceutical composition comprising said peptide and optionally, said p53 inhibitor.

32. A method of treating cancer in a subject comprising contacting the subject with a peptide according to claim 1.

33. A method of treating cancer in a subject comprising contacting the subject with a peptide according to claim 1, and a p53 inhibitor as a combined preparation for simultaneous, separate or sequential use in the treatment of a cancer containing cells that express wild type p53.

34. The method of claim 32, wherein the cancer is selected from the group consisting of: breast cancer, prostate cancer, colorectal cancer, bladder cancer, ovarian cancer, endometrial cancer, cervical cancer, head and neck cancer, stomach cancer, pancreatic cancer, esophageal cancer, small cell lung cancer, non-small cell lung cancer, malignant melanoma, neuroblastoma, leukaemia, lymphoma, sarcoma and glioma.

35. A pharmaceutical composition according to claim 28, further comprising stem cells.

* * * * *